United States Patent
Fritchie et al.

(10) Patent No.: US 10,648,905 B2
(45) Date of Patent: May 12, 2020

(54) SYSTEMS, APPARATUS, AND RELATED METHODS FOR EVALUATING BIOLOGICAL SAMPLE INTEGRITY

(71) Applicant: Abbott Laboratories, Abbott Park, IL (US)

(72) Inventors: Patrick Fritchie, Southlake, TX (US); Michael Shawn Murphy, Allen, TX (US); Michael Cobert, McKinney, TX (US)

(73) Assignee: ABBOTT LABORATORIES, Abbott Park, IL (US)

(*) Notice: Subject to any disclaimer, the term of this patent is extended or adjusted under 35 U.S.C. 154(b) by 0 days.

(21) Appl. No.: 15/693,151

(22) Filed: Aug. 31, 2017

(65) Prior Publication Data

US 2018/0059006 A1     Mar. 1, 2018

Related U.S. Application Data

(60) Provisional application No. 62/381,792, filed on Aug. 31, 2016.

(51) Int. Cl.
*G01N 21/00*     (2006.01)
*G01N 33/00*     (2006.01)
(Continued)

(52) U.S. Cl.
CPC .......... *G01N 21/255* (2013.01); *G01N 21/00* (2013.01); *G01N 21/27* (2013.01); *G01N 33/483* (2013.01);
(Continued)

(58) Field of Classification Search
None
See application file for complete search history.

(56) References Cited

U.S. PATENT DOCUMENTS 5,276,316 A * 1/1994 Blanford .............. G06K 7/1491
                                                          235/462.12
5,672,317 A * 9/1997 Buhler .............. G01N 35/00732
                                                          422/65
(Continued)

FOREIGN PATENT DOCUMENTS

DE         19911351         9/2000
DE       202013102120       6/2013
(Continued)

OTHER PUBLICATIONS

International Searching Authority, "International Search Report and Written Opinion," issued in connection with application No. PCT/US2017/049657, dated Oct. 23, 2017, 16 pages.

(Continued)

*Primary Examiner* — Kara E. Geisel
*Assistant Examiner* — Jarreas C Underwood
(74) *Attorney, Agent, or Firm* — Hanley, Flight & Zimmerman, LLC

(57) ABSTRACT

Systems, apparatus, and related methods for evaluating biological sample integrity are disclosed herein. An example method includes scanning a sample container having a sample disposed therein to generate signal data including a first signal portion and a second signal portion. The example method includes detecting if the sample container includes a label attached to a surface of the sample container based on the second signal portion. If the sample container includes a label, the example method includes applying an adjustment factor to the second signal portion to create adjusted signal data. The example method includes determining a property of the sample based on one or more of the first signal portion or the adjusted signal data.

20 Claims, 17 Drawing Sheets

(51) Int. Cl.
*G01N 21/25* (2006.01)
*G06Q 50/22* (2018.01)
*G01N 21/27* (2006.01)
*G01N 33/483* (2006.01)
*G01N 35/10* (2006.01)

(52) U.S. Cl.
CPC ......... *G06Q 50/22* (2013.01); *G01N 35/1011* (2013.01); *G01N 2201/10* (2013.01); *G01N 2201/12* (2013.01)

(56) References Cited

U.S. PATENT DOCUMENTS

| | | | |
|---|---|---|---|
| 5,879,628 A | | 3/1999 | Ridgeway et al. |
| 6,002,474 A | | 12/1999 | Thomas et al. |
| 6,120,942 A | * | 9/2000 | Reinberg ............... G03F 1/38 216/12 |
| 6,260,764 B1 | | 7/2001 | Zocca et al. |
| 6,267,927 B1 | | 7/2001 | Pomar Longedo et al. |
| 6,388,750 B1 | | 5/2002 | Liu et al. |
| 6,450,227 B1 | * | 9/2002 | Labardi ............... B65C 9/1865 156/351 |
| 6,473,190 B1 | | 10/2002 | Dosmann |
| 6,628,395 B2 | | 9/2003 | Liu et al. |
| 6,711,516 B2 | | 3/2004 | Samsoondar |
| 6,770,883 B2 | * | 8/2004 | McNeal ............... G01F 23/292 250/341.1 |
| 6,891,182 B2 | | 5/2005 | Watari et al. |
| 7,271,912 B2 | | 9/2007 | Sterling et al. |
| 7,545,972 B2 | | 6/2009 | Itoh |
| 7,593,108 B2 | | 9/2009 | Sterling et al. |
| 7,618,586 B2 | | 11/2009 | Saito et al. |
| 7,688,448 B2 | | 3/2010 | Bamberg et al. |
| 7,782,447 B2 | | 8/2010 | Lindberg |
| 7,951,059 B2 | | 5/2011 | Sweat |
| 8,030,948 B2 | | 10/2011 | Manneschi |
| 8,070,663 B2 | | 12/2011 | Sweat |
| 8,116,428 B2 | | 2/2012 | Gudmundson et al. |
| 8,170,271 B2 | * | 5/2012 | Chen ............... G01N 35/00732 382/100 |
| 8,525,989 B2 | | 9/2013 | Iguchi et al. |
| 8,781,066 B2 | | 7/2014 | Gudmundson et al. |
| 8,973,736 B2 | | 3/2015 | Johns et al. |
| 8,996,338 B2 | | 3/2015 | Xu et al. |
| 9,046,506 B2 | | 6/2015 | Müller et al. |
| 9,080,962 B1 | * | 7/2015 | Manneschi ......... G01N 21/3577 |
| 9,146,247 B2 | | 9/2015 | Zahniser et al. |
| 9,194,785 B2 | * | 11/2015 | Bentien ............. G01N 15/1459 |
| 9,261,449 B2 | | 2/2016 | Itoh |
| 9,322,761 B2 | | 4/2016 | Miller |
| 9,335,260 B2 | | 5/2016 | Manneschi |
| 9,446,418 B2 | | 9/2016 | Johns et al. |
| 9,470,510 B2 | | 10/2016 | Wilson et al. |
| 9,482,684 B2 | | 11/2016 | Johns et al. |
| 9,494,417 B2 | | 11/2016 | Stefan |
| 9,506,943 B2 | | 11/2016 | Müller et al. |
| 9,551,656 B2 | | 1/2017 | Xu et al. |
| 9,599,546 B2 | | 3/2017 | Small et al. |
| 9,785,754 B2 | | 10/2017 | Pedrazzini |
| 9,880,082 B2 | * | 1/2018 | Esaki ............... G01N 33/491 |
| 9,983,192 B2 | * | 5/2018 | Klinec ............... G01N 33/49 |
| 2002/0089669 A1 | | 7/2002 | Liu et al. |
| 2002/0134923 A1 | * | 9/2002 | Watari ............... G01B 11/028 250/221 |
| 2002/0139851 A1 | * | 10/2002 | Hecht ............... G06K 7/10851 235/454 |
| 2004/0066507 A1 | * | 4/2004 | Kren ............... G01N 21/9501 356/237.4 |
| 2004/0086173 A1 | | 5/2004 | Itoh |
| 2006/0153737 A1 | | 7/2006 | Saito et al. |
| 2007/0025505 A1 | * | 2/2007 | Bjorkholm ............. G01N 23/04 378/53 |
| 2008/0100851 A1 | | 5/2008 | Asfour et al. |
| 2008/0178653 A1 | * | 7/2008 | Gunstream .......... C12Q 1/6851 73/1.02 |
| 2008/0297769 A1 | * | 12/2008 | Bamberg ............... G01N 21/31 356/73 |
| 2009/0117620 A1 | * | 5/2009 | Fritchie ................. B01L 3/5085 435/91.1 |
| 2009/0153836 A1 | | 6/2009 | Lindberg |
| 2011/0145006 A1 | | 6/2011 | Pedrazzini |
| 2012/0140230 A1 | * | 6/2012 | Miller ................. G01N 15/042 356/441 |
| 2013/0021461 A1 | | 1/2013 | Zahniser et al. |
| 2013/0076882 A1 | * | 3/2013 | Itoh ........................ G01N 21/25 348/77 |
| 2013/0123089 A1 | | 5/2013 | Johns et al. |
| 2013/0125648 A1 | | 5/2013 | Murashie et al. |
| 2013/0125675 A1 | | 5/2013 | Müller et al. |
| 2013/0126302 A1 | | 5/2013 | Johns et al. |
| 2013/0128035 A1 | | 5/2013 | Johns et al. |
| 2013/0129166 A1 | | 5/2013 | Müller et al. |
| 2013/0143257 A1 | | 6/2013 | Small et al. |
| 2013/0243653 A1 | | 9/2013 | Koiso et al. |
| 2013/0260448 A1 | | 10/2013 | Wilson et al. |
| 2014/0036276 A1 | | 2/2014 | Gross et al. |
| 2014/0103674 A1 | | 4/2014 | Mueller et al. |
| 2014/0105719 A1 | | 4/2014 | Mueller et al. |
| 2014/0107953 A1 | | 4/2014 | Mueller et al. |
| 2014/0305227 A1 | | 10/2014 | Johns |
| 2015/0238978 A1 | | 8/2015 | Müller et al. |
| 2015/0241457 A1 | | 8/2015 | Miller |
| 2016/0018427 A1 | * | 1/2016 | Streibl ............. G01N 35/00584 702/19 |
| 2016/0109350 A1 | | 4/2016 | Esaki et al. |
| 2016/0135761 A1 | * | 5/2016 | Lou ........................ A61B 6/032 378/162 |
| 2016/0349237 A1 | | 12/2016 | Klinec et al. |
| 2016/0349278 A1 | | 12/2016 | Johns et al. |
| 2017/0001813 A1 | | 1/2017 | Wilson et al. |

FOREIGN PATENT DOCUMENTS

| | | |
|---|---|---|
| EP | 0185285 | 6/1986 |
| EP | 1243892 | 9/2002 |
| EP | 1293256 | 3/2003 |
| EP | 2293028 | 3/2011 |
| JP | 2005017219 | 1/2005 |
| JP | 2009115534 | 5/2009 |
| JP | 5033675 | 9/2012 |
| WO | 2013070716 | 5/2013 |
| WO | 2013070744 | 5/2013 |
| WO | 2013070755 | 5/2013 |
| WO | 2013070756 | 5/2013 |
| WO | 2014025817 | 2/2014 |
| WO | 2014031576 | 2/2014 |
| WO | WO 2015124512 * | 2/2015 |
| WO | 2015124512 | 8/2015 |

OTHER PUBLICATIONS

Wikipedia, "Automated Pipetting System," retrieved Jan. 16, 2017, from <https://en.wikipedia.org/w/index.php?title=Automated_pipetting_system&oldid=546409661>, 3 pages.
Wikipedia, "Color Space," retrieved Jan. 4, 2018, from <https://en.wikipedia.org/wiki/Color_space>, 7 pages.
Wikipedia, "List of Color Spaces and Their Uses," retrieved Jan. 4, 2018, from <https://en.wikipedia.org/wiki/List_of_color_spaces_and_their_uses>, 5 pages.
The International Bureau of WIPO, "International Preliminary Report on Patentability," issued in connection with International Application No. PCT/US2017/049657, dated Mar. 5, 2019, 9 pages.
European Patent Office, "Communication Pursuant to Article 94(3) EPC," issued in connection with Euroepan application No. 17768894.2, dated Jan. 29, 2020, 7 pages.

* cited by examiner

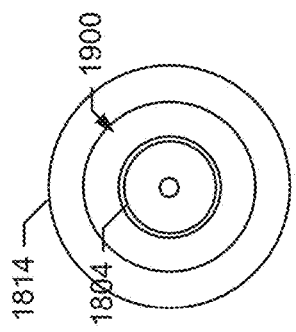
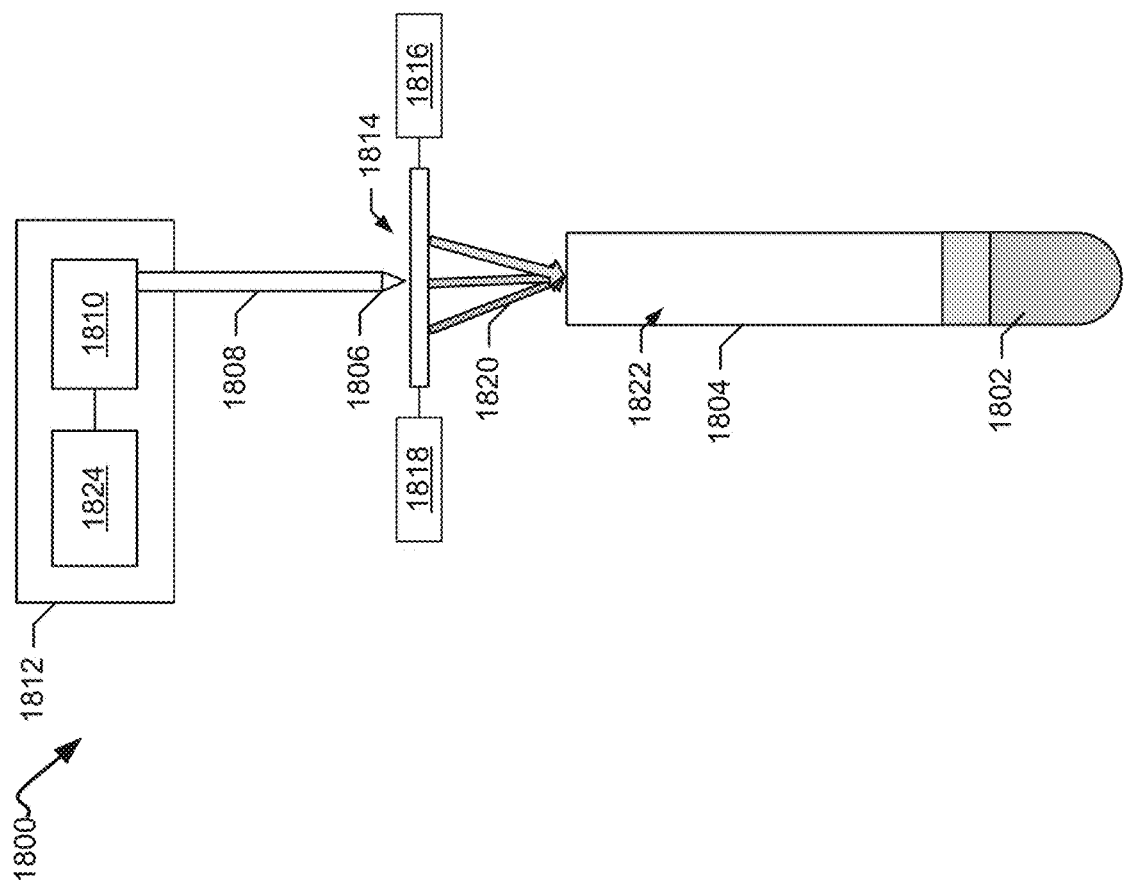

US 10,648,905 B2

SYSTEMS, APPARATUS, AND RELATED METHODS FOR EVALUATING BIOLOGICAL SAMPLE INTEGRITY

RELATED APPLICATION

This patent claims the benefit under 35 U.S.C. § 119(e) to U.S. Provisional Patent Application No. 62/381,792, filed Aug. 31, 2016, which is incorporated hereby incorporated by reference in its entirety.

FIELD OF THE DISCLOSURE

This disclosure relates generally to analysis of biological samples, and, more particularly, to systems, apparatus, and related methods for evaluating biological sample integrity.

BACKGROUND

Integrity of a biological sample (e.g., an adequacy of a sample for processing based on one or more characteristics or properties of the sample or the container in which the sample is disposed) can affect the processing of the sample and the analysis of the results obtained from the processing. Laboratory procedures often include checking a biological sample with respect to properties such as sample color and sample volume to determine the quality of sample. For example, a blood sample may be reviewed with respect to hemoglobin content as indicated by an intensity of a red color of the sample. An evaluation of the integrity of the biological sample can also include verifying a proper cap color of a container in which the sample is disposed, which can indicate sample type, testing procedures to be performed, and/or represent other codes related to handling of the sample.

BRIEF DESCRIPTION OF THE DRAWINGS

FIG. 18 is a schematic, side view illustration of another example system for evaluating sample integrity that can be used to implement the examples disclosed herein FIG. 19 is a schematic, top view of a portion of the example system of FIG. 18.

The figures are not to scale. Instead, to clarify multiple layers and regions, the thickness of the layers may be enlarged in the drawings. Wherever possible, the same reference numbers will be used throughout the drawing(s) and accompanying written description to refer to the same or like parts.

DETAILED DESCRIPTION

Figure 1:
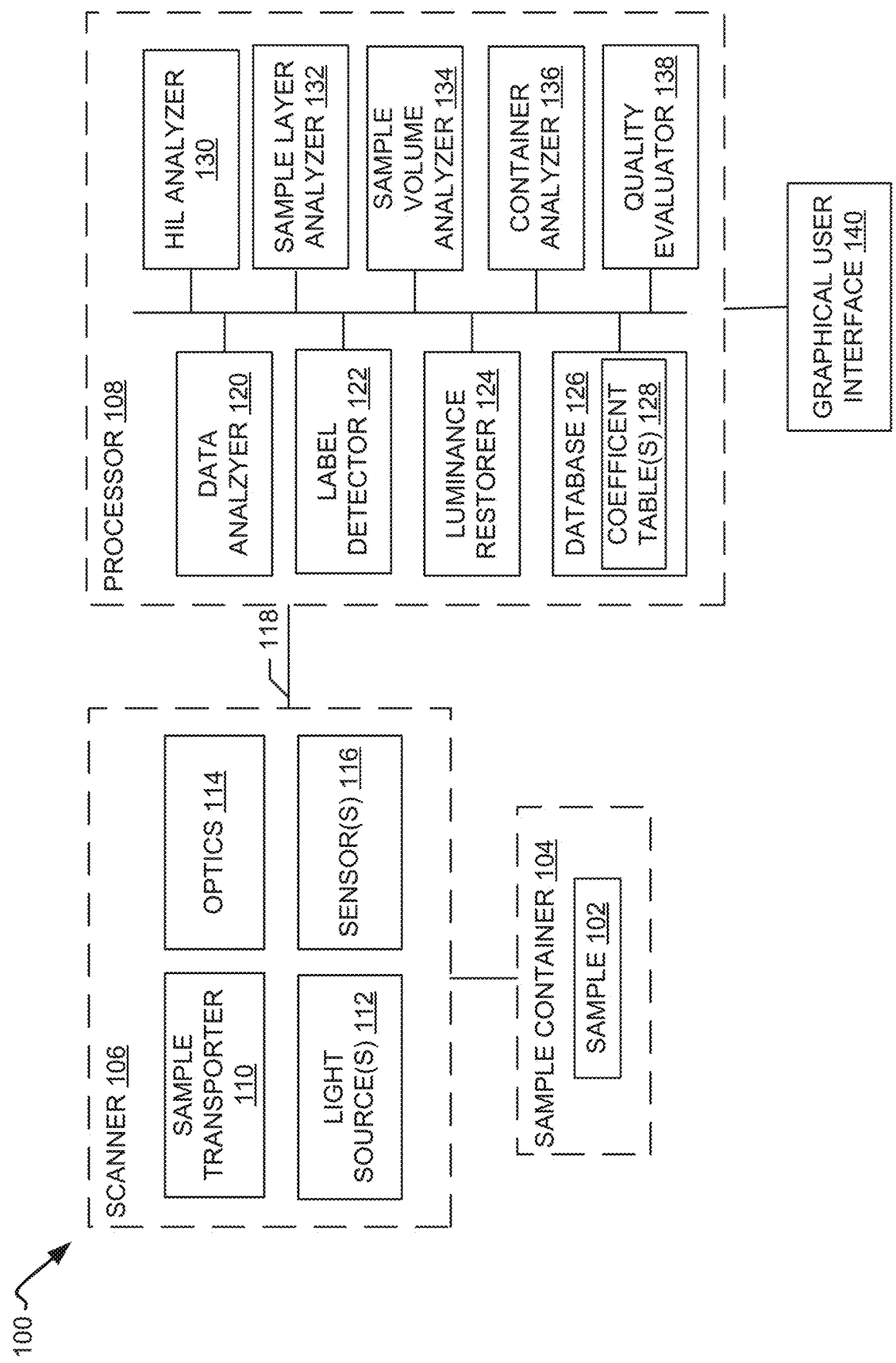
FIG. 1 is a block diagram of an example system for evaluating sample integrity that can be used to implement the examples disclosed herein.

Methods, systems, and apparatus for determining biological sample integrity are disclosed herein. Before, during, and/or after collection and/or processing of a biological sample (hereinafter generally referred to as "a sample" or "the sample"), the sample is typically checked with respect to sample properties such as sample color. For example, the color of a blood sample may be inspected for detection of (1) hemolysis, or a rupture of red blood cells that results in a release of hemoglobin from the red blood cells into the blood plasma and gives the sample a reddish color; (2) icterus, or an excess of bilirubin in the sample, which is indicated by a yellowish color; and (3) lipemia, or a high concentration of lipids (e.g., fats) in the sample that give the sample a white, milky color.

An analysis for hemolysis, icterus, and lipemia (hereinafter collectively referred to as "HIL") is performed to identify whether there are any conditions in the sample that may affect testing of the sample and/or the results obtained. For example, a presence of hemolysis in a sample can affect test results, as the ruptured red blood cells contaminate surrounding plasma. HIL analysis also serves as an indicator of sample processing quality. For example, hemolysis can indicate problems during collection of the sample from a subject, such as excessive suctioning, incorrect needles size, etc. Hemolysis may also reflect mishandling of the container in which the sample is disposed, such as improper tube mixing or heating of the sample tube above a temperature threshold. Thus, color analysis of the sample can provide information related to sample quality and can be used to determine if testing of the sample should proceed or if the sample should be treated as an exception.

A sample may also be checked to ensure that there is sufficient volume for processing the sample using a clinical analyzer or another laboratory apparatus. For example, a volume of plasma or serum above a separator gel or a buffy coat in a sample tube can indicate whether there is sufficient sample volume for testing. As another example, a volume of plasma or serum at a bottom of the tube for an aliquot sample (e.g., a sample spilt into parts) can be used to indicate whether the sample volume is sufficient for testing. Sample volume can also be determined based on an amount of sample versus air in the sample container.

A sample that has undergone centrifugation may also be reviewed to evaluate a quality or an efficacy of the centrifugation. A sample that has been adequately separated as a result of centrifugation exhibits well-defined or clear borders between layers of the sample. Inadequacies in the centrifugation process can be indicated by, for example, a sample that has been centrifuged but is lacking sharp borders between layers or has a cloudiness or haziness in certain layers, which may indicate impurities in one or more layers.

As another example, a sample may be checked for a presence of microclots in the sample. For example, microclots can form as a result of leaving a blood sample in a syringe too long before placing the sample in a sample tube, as coagulation begins after the blood is drawn from a subject. Microclots can also form as a result of improper mixing and/or inversion of a sample tube including the blood sample and an anticoagulant.

Properties of the container in which the sample is disposed are also examined as part of verifying an integrity of the sample. For example, a color of a cap of a test tube in which the sample is disposed can indicate whether the sample should be centrifuged or not, what tests the sample should undergo, whether the sample should be stored, etc. Thus, verifying that the sample tube includes the correctly colored cap is important with respect to proper handling of the sample.

Sample checking can be performed by, for example, laboratory personnel who may make qualitative assessments about the integrity of the sample by looking at the sample and/or the sample container. Evaluations of sample color can be performed by a laboratory assistant who visually inspects the sample to evaluate, for example, the intensity of the red color of the sample as a measure of hemoglobin content as part of a HIL analysis. The laboratory assistant may also perform a turbidity test to evaluate a cloudiness of the sample or one or more layers of the sample based on impurities that are visible to the human eye to evaluate centrifugation quality. A color of a cap of the sample container can also be checked against a test plan for the sample by the laboratory assistant to verify that the sample container is appropriately marked.

Some known methods for automating the sample checking process performed by laboratory personnel include performing HIL analysis by measuring color absorption. For example, a sample may be aspirated from a test tube and disposed in an analyzer to measure color absorption and to determine HIL concentrations based on the results of the color absorption analysis. However, opening the sample tube increases processing time as well as the risk of sample contamination. Further, although some known methods use optics to determine HIL values without sample aspiration via wavelength spectroscopy, such known methods often require precise placement of the sample tube in an analyzer to accommodate labels affixed to the sample tube. A label on the sample tube can interfere with the results obtained from wavelength spectroscopy if the sample tube is not properly oriented and light waves are directed through the label. Properties of the sample and/or the sample container can also be analyzed via image processing of sample images captured using cameras, however, such techniques are limited with respect to pixel quality and require consideration of positioning of the sample container to account for labels.

Disclosed herein are example methods, systems, and apparatus for performing automated sample integrity checking using signal data collected by scanning a sample in a sample container. In particular, the examples disclosed herein use light emitting diodes (LEDs) and/or lasers and detectors to provide qualitative assessments of sample properties such as color, volume, and sample layer separation. The disclosed examples provide such assessments without requiring aspiration of the sample from the container, thereby saving time and reducing contamination risks as compared to methods that involve open-tube sampling. The disclosed examples also analyze properties of the sample container such as a color of a cap on the container based on the signal data.

The disclosed examples do not require precise orientation of the sample container in an analyzer to adjust for labels on the container. Rather, the disclosed examples automatically adjust for the presence of one or more labels on the sample tube using one or more algorithms that dynamically restore or interpolate signal data collected during scanning of the sample container and attenuated due to the presence of the label on the container. The disclosed examples do not require the sample container to be positioned to avoid interference from the label(s) during scanning of the sample container, thereby increasing efficiency with respect to the sample integrity checking process. The disclosed examples reduce time and costs while increasing accuracy of the sample integrity analysis as compared to visual checks by laboratory personnel. The disclosed examples generate quality indicators that classify a sample as ready for testing or as requiring exception or special handling. Such quality indicators can be displayed to a user via a graphical user interface for further action with respect to processing of the sample.

Also disclosed herein are example methods, systems, and apparatus for performing automated sample integrity checking using signal data collected by emitting light into an open sample container or a sample container that does not include a cap or other covering. In some disclosed examples, the evaluation of the sample disposed in the open sample container can be used to determine whether the sample is acceptable for aspiration by a pipettor. In some disclosed examples, a position of the pipettor is controlled based on the sample quality analysis.

An example method includes scanning, by executing an instruction with a processor, a sample container having a sample disposed therein to generate signal data including a first signal portion and a second signal portion. The example method includes detecting, by executing an instruction with the processor, if the sample container includes a label attached to a surface of the sample container based on the second signal portion. If the sample container includes a label, the example method includes applying, by executing an instruction with the processor, an adjustment factor to the second signal portion to create adjusted signal data. The example method includes determining, by executing an instruction with the processor, a property of the sample based on one or more of the first signal portion or the adjusted signal data.

In some examples, the method includes assigning a quality indicator to the sample based on the property of the sample.

In some examples, the property is one of a level of hemolysis, icterus, or lipemia in the sample.

In some examples, the method includes generating a representation of the sample based on the adjusted signal data. In some such examples, the property is a sample color and the representation includes the property.

In some examples, detecting if the sample container includes a label includes identifying attenuated signal data in the second signal portion and determining if the attenuated signal data is below a predetermined threshold. In such examples, if the attenuated signal data is below the threshold, the method includes determining that the sample container includes the label.

In some examples, the method includes determining a number of labels on the sample container based on the attenuated signal data relative to non-attenuated signal data for the sample container or a second sample container.

In some examples, the method includes retrieving the adjustment factor from a database based on the signal data.

In some examples, the first signal portion and the second signal portion are substantially the same.

Another example method includes scanning, by executing an instruction with a processor, a sample container to generate signal data. At least a portion of the sample container contains a sample. The method includes detecting, by executing an instruction with the processor, an attenuated portion in the signal data and restoring the attenuated portion of the signal data to generate a restored portion. The method includes determining, by executing an instruction with the processor, a property of the sample based on the signal data including the restored portion.

In some examples, restoring the attenuated portion of the signal data includes identifying a value in at least one of the attenuated portion or the signal data not including the attenuated portion and performing a comparison of the value to previously known values stored in a database. In such examples, the method includes identifying a signal restoration coefficient based on the comparison and applying the signal restoration coefficient to the attenuated portion to generate the restored portion. In some such examples, the attenuated portion is due to a presence of at least one label on the sample container and the method further includes identifying the signal restoration coefficient based on a number of labels on the sample container In some examples, the method includes interpolating the restored portion in the signal data.

In some examples, the signal data includes first signal data corresponding to a first color and second signal data corresponding to a second color. In such examples, restoring the attenuated portion of the signal data includes restoring a first attenuated portion in the first signal data and restoring a second attenuated portion in the second signal data.

In some examples, scanning the sample container includes exposing at least a portion of the sample container to a light source. In such examples, the method includes determining a luminance percentage of an output of the light source and generating a representation of the sample based on the signal data, the restored portion, and the luminance percentage.

An example system disclosed herein includes a scanner to scan a sample container having a sample disposed therein, the scan to generate signal data. The example system includes a processor to detect a presence of a label on the sample container based on the signal data. The processor is to restore at least a portion of the signal data based on the detection of the label and identify the sample as a routine sample or as an exception based on the signal data including the restored portion of the signal data.

In some examples, the scanner is to identify a position of a cap coupled to the sample container based on the signal data. The scanner is to move the sample container to expose the cap of the sample container to a light source. In such examples, the processor is to determine a color of the cap.

In some examples, the processor is to generate an indicator representing the sample as being a routine sample or an exception and output the indicator for viewing via a graphical user interface.

In some examples, the processor is to restore the portion of the signal data by comparing the portion of the signal data to calibration data, determining a signal restoration coefficient based on the comparison, and applying the signal restoration coefficient to the portion to generate the restored portion.

In some examples, the signal data is indicative of a color of the sample and the processor is to analyze one or more of a hemolysis level, an icterus level, or a lipemia level in the sample based on the color of the sample and identify the sample as an exception if at least one of the hemolysis level, the icterus level, or the lipemia level is above a respective threshold.

In some examples, the signal data is indicative of a color of the sample and the processor is to identify a first layer in the sample and a second layer in the sample based on the color of the sample and identify the sample as an exception based on a color of one or more of the first layer, the second layer, or a border between the first layer and the second layer.

In some examples, the processor is to detect the presence of the label on the sample container by identifying a change in a first portion of the signal data relative to a second portion of the signal data and detecting the presence of a label on the sample container based on the identification of the change in the first portion of the signal data.

In some examples, the scanner includes a first array and a second array disposed about the sample container. Each of the first array and the second array include a light emitter and a sensor. In some such examples, the first array and the second array are disposed within a first plane relative to a portion of the sample container. The sensor of at least one of the first array or the second array is to generate signal data for the portion of the sample container. In some such examples, the processor is to identify the sample as a routine sample or as an exception based on the signal data for the portion of the sample container.

An example method disclosed herein includes exposing, by executing an instruction with a processor, a sample disposed in a sample container to light. The sample container is decapped. The example method includes generating, by executing an instruction with the processor, signal data based on the exposure of the sample to the light and controlling, by executing an instruction with the processor, a position of a pipettor relative to the sample based on the signal data.

In some examples, the method includes determining if the sample is to be aspirated via the pipettor based on the signal data. The controlling of the position of the pipettor is to be based on the analysis.

In some examples, the exposing of the sample to the light includes emitting a light beam into an interior of the sample container and the generating of the signal data includes detecting the light reflected by the sample. In some such examples, the emitting of the light is to be performed by a light emitter and the generating of the signal is to be performed by a sensor. The light emitter and the sensor are to be disposed on an array In some examples, the controlling of the position of the pipettor includes moving the pipettor relative to the sample container to cause the pipettor to engage the sample based on the signal data.

FIG. 1 is a block diagram of an example system 100 for determining properties of a sample 102 (e.g., sample volume, sample color) disposed in a sample container 104 and/or properties of the sample container 104 (e.g., container cap color) for assessing an adequacy of the sample for processing. The sample container 104 can be, for example, a test tube. At least a portion of the sample container 104 contains the sample 102. For example purposes, the sample 102 discussed herein will be described as a blood sample; however, other biological samples can also be used with the example system 100 of FIG. 1.

To determine properties of the sample 102 and/or the sample container 104, the sample container 104 containing the sample 102 is disposed in a scanner 106. In some examples, the scanner 106 is disposed in a clinical analyzer or other laboratory apparatus. In other examples, the scanner 106 is separate from the analyzer (e.g., as disclosed below in connection with FIG. 16). The scanner 106 scans the sample container 104 and, thus, the sample 102 disposed therein, to collect data about the sample 102 and/or the sample container 104. The scanner 106 is communicatively coupled to a processor 108 for controlling scanning of the sample container 104 and storing and analyzing the resulting data obtained from the scan(s), as will be further disclosed below.

In the example system 100 of FIG. 1, the sample container 104 is disposed in or supported by a sample transporter 110 of the scanner 106. The sample transporter 110 includes a platform, holder, or other structure for receiving and supporting the sample container 104 in the scanner 106. The sample container 104 can be placed in the sample transporter 110 by, for example, a user or a robotic machine. In the examples disclosed herein, the sample container 104 can be placed in the sample transporter 110 without any restrictions on orientation of the sample container 104 with respect to a label affixed to the sample container 104 relative to other components of the scanner 106.

The example scanner 106 includes one or more light sources 112. The light source(s) 112 include, for example, an array of light emitting diodes (LEDs). The LED array emits individual colors of light (e.g., red, green, blue). In some examples, the light source(s) 112 include two or more LED arrays. In other examples, the light source(s) 112 include an LED array that emits individual colors of light into a reflective light pipe, which emits the light as a single color. In other examples, the light source(s) 112 include one or more arrays of lasers.

The light source(s) 112 emit a light that is directed toward the sample container 104 disposed in the sample transporter 110. The light can be in the form of one or more light beams having a wavelength corresponding to colors such as red light (e.g., light having a wavelength between about 620-750 nm), green light (e.g., light having a wavelength between about 495-570 nm), blue light (e.g., light having a wavelength between about 450-495 nm), or other colors, such as, for example, yellow light. In some examples, the light source(s) 112 emit infrared waves. In other examples, the light source(s) 112 emit light having wavelengths other than wavelengths associated with infrared light. The light source(s) 112 are oriented relative to the sample transporter 110 such that the light emitted by the light source(s) 112 pass through the sample container 104 disposed in the sample transporter 110.

The example system 100 also includes optics 114. The example optics 114 of FIG. 1 include one or more lens. The optics 114 focus the light from the light source(s) 112 to avoid, for example, shadows that may result from transmission of light as a single beam. The optics 114 can also focus the light that passes through the sample container 104 for detection by one or more sensors 116 of the scanner 106. The sensor(s) 116 of the scanner 106 can include, for example, an infrared sensor to measure the infrared light (e.g., light have a wavelength longer than 800 nm, such as, for example 950 nm) passing through the sample container 104. The sensor(s) 116 can include a digital color sensor to detect colors of the light passing through the sample container 104 and/or the sample 102, including red light, green light, and blue light as well as clear light, a combination of the red, green, and blue ("RGB") colors together, or light having a wavelength corresponding to other colors (e.g., yellow light). In some examples, the sensor(s) 116 are high-definition sensors (e.g., sensors having increased signal reading capabilities as compared to non-high-definition sensors) that allow for the detection of at least a portion of light that encounters a label disposed on the sample container 104, as will be disclosed below. In some examples, the sensor(s) 116 include XYZ color sensor(s). More generally, the sensor(s) 116 can include color sensor(s) (e.g., digital sensor(s)) that can detect and output values associated with one or more color space models, such as an RGB color model, a CIE XYZ color model, etc. The sensor(s) 116 can be calibrated based on the color space model(s). The sensor(s) 116 can include a sensor board. The sensor(s) 116 provide a signal output representative of the detected light.

The processor 108 of the example system 100 of FIG. 1 receives signal data including sample light measurements from the sensor(s) 116 via a communication link 118. The processor 108 analyzes one or more properties of the sample 102 and/or the sample container 104 based on the data received from the sensor(s) 116. In some examples, the signal data is received from the sensor(s) 116 is digital data. In other examples, the processor 108 converts analog signal data to digital data via an analog-to-digital converter. The processor 108 includes a data analyzer 120 to process the data received from the sensor(s) 116. For example, the data analyzer 120 can generate graphical representations of the signal data.

In some examples, the light emitted by the light source(s) 112 passes through one or more labels on the sample container 104. The processor 108 includes a label detector 122 to detect the presence of the one or more labels on the sample container 104 based on the signal data received from the sensor(s) 116. The processor 108 also includes a luminance restorer 124 to correct for the presence of the label(s) in the data, as will be disclosed below.

The processor 108 includes a database 126 to store data related to the processing of the signal data. The database 126 also stores data that is used by the luminance restorer 124 to account for the presence of the label(s). The database 126 includes one or more coefficient tables 128 that store adjustment factors or signal restoration coefficients used by the luminance restorer 124 to account for an effect of the label(s) on the signal data.

The processor 108 includes a HIL analyzer 130 to analyze the sample data with respect to hemolysis, icterus, and lipemia, a sample layer analyzer 132 to analyze centrifugation efficacy based on properties of layers in the sample, a sample volume analyzer 134 to identify whether or not the sample 102 has sufficient volume for testing, and a container analyzer 136 to determine the color of the cap of the sample container 104. The processor 108 also includes a quality evaluator 138 to provide an output indicative of a quality of the sample 102 for further processing.

In the example system 100, a user interacts with the processor 108 via a graphical user interface 140. In some examples, data provided by the user via the graphical user interface 140, such as intended testing for the sample 102 is stored in the database 126. The user can also view the quality indicator output by the quality evaluator 138 via the graphical user interface 140.

Figure 2:
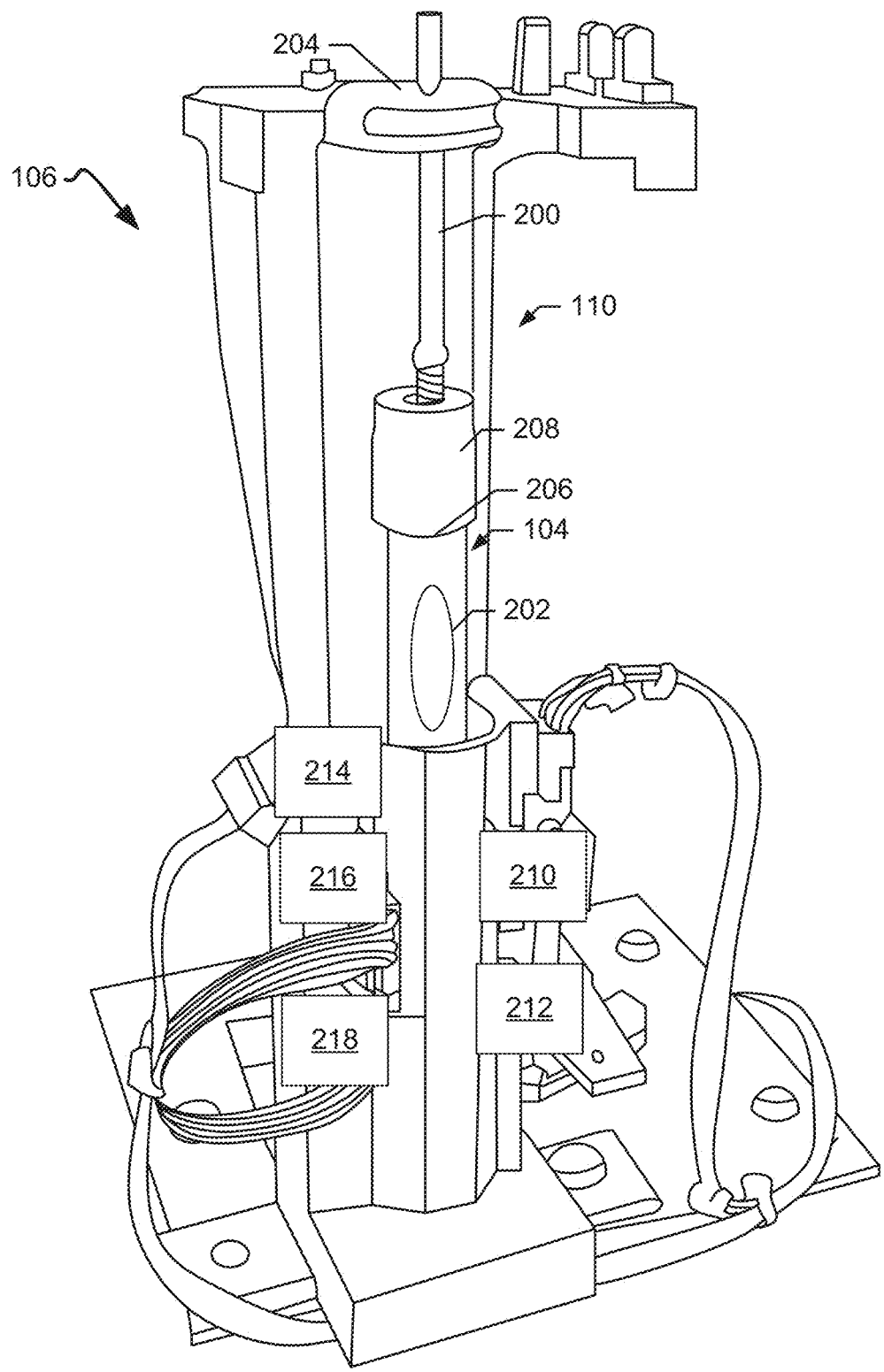
FIG. 2 is right, perspective view of an example scanner for use in connection with the example system of FIG. 1.

FIG. 2 is a perspective view of the example scanner 106 of the example system 100 of FIG. 1, including a sample container 104 disposed in the sample transporter 110. As shown in FIG. 2, the sample transporter 110 includes a sample container support 200 that receives a portion of the sample container 104 and supports the sample container 104 during scanning. When the sample container 104 is disposed in the sample transporter 110, at least a portion (e.g., a substantial portion) of the sample container 104 remains exposed or uncovered for scanning of the sample container 104 and the sample 102. As shown in FIG. 2, a label 202 is affixed to a portion of the sample container 104. The sample container 104 can include additional labels 202 affixed to a surface of the sample container 104.

In some examples, the sample transporter 110 includes a drive mechanism 204 (e.g., a motor) that moves the sample container support 200 with the sample container 104 along a longitudinal axis of the sample transporter 110. The drive mechanism 204 moves the sample container support 200 and, thus, the sample container 104, over a predetermined distance range along the longitudinal axis of the sample transporter 110 from a predetermined starting or loading position of the sample container support 200. For example, the drive mechanism 204 can move the sample tube support 120 millimeters or more from the loading position of the sample container support 200. In some examples, the distance over which the drive mechanism 204 moves the sample container support 200 is based on a height of the sample container 104 and/or a height of the sample 102 (e.g., a liquid) in the sample container 104. For example, an edge 206 of a sample container stopper 208 disposed in the sample container 104 can be used as a reference point for a level of the sample 102 in the sample container 104 and, thus, as a reference point for the distance range over which the drive mechanism 204 moves the sample container support 200. Thus, the sample transporter 110 serves as an elevator for the sample container 104.

To scan the sample container 104 disposed in the sample container support 200 of the sample transporter 110, the drive mechanism 204 moves the sample container support 200 along the longitudinal axis of the sample transporter 110 past the light source(s) 112. The scanner 106 scans the sample container 104 from a bottom of the sample container 104 (e.g., the portion of the sample container 104 opposite the stopper 208) to a top of the sample container 104 (e.g., the portion of the sample container 104 with the stopper 208). In other examples, the scanner 106 scans a portion of the sample container 104. As the sample container 104 moves past the light source(s) 112, light emitted from the light source(s) 112 is transmitted to and passes through the exposed portions of the sample container 104 and, thus, the sample 102, along the longitudinal axis of the sample container 104. In some examples, the label 202 of the sample container 104 is in a transmission path of the light emitted by the light source(s) 112.

For example, the light source(s) 112 of the example scanner 106 include a first LED 210 that emits red, green, and blue lights (e.g., an RGB array), a second LED 212 that emits infrared signals, and a third LED 214 that emits white light or full spectrum white light. In some examples, one or more LEDS (e.g., the third LED 214) emitting white light, full spectrum white light, or an RBG array are used to detect a color of the stopper 208 of the sample container 104. In some examples, the drive mechanism 204 moves the sample container 104 past the light source(s) 112 two or more times to perform multiple scans of the sample container 104 and the sample 102. The drive mechanism 204 of the example sample transporter 110 moves the sample container support 200 at a constant speed. As a result, data collected by the sensor(s) 116 during each scan can be associated with certain locations of the sample container 104. For example, the scanner 106 of FIG. 2 includes a first sensor 216 to detect the red, green, and blue light emitted by the first LED 210 and passing through the sample container 104 (and, at some locations, the sample 102). The scanner 106 also includes a second sensor 218 to detect the infrared signals emitted by the second LED 212 passing through the sample 102 and the sample container 104 (and, at some locations, the sample 102).

Figure 3:
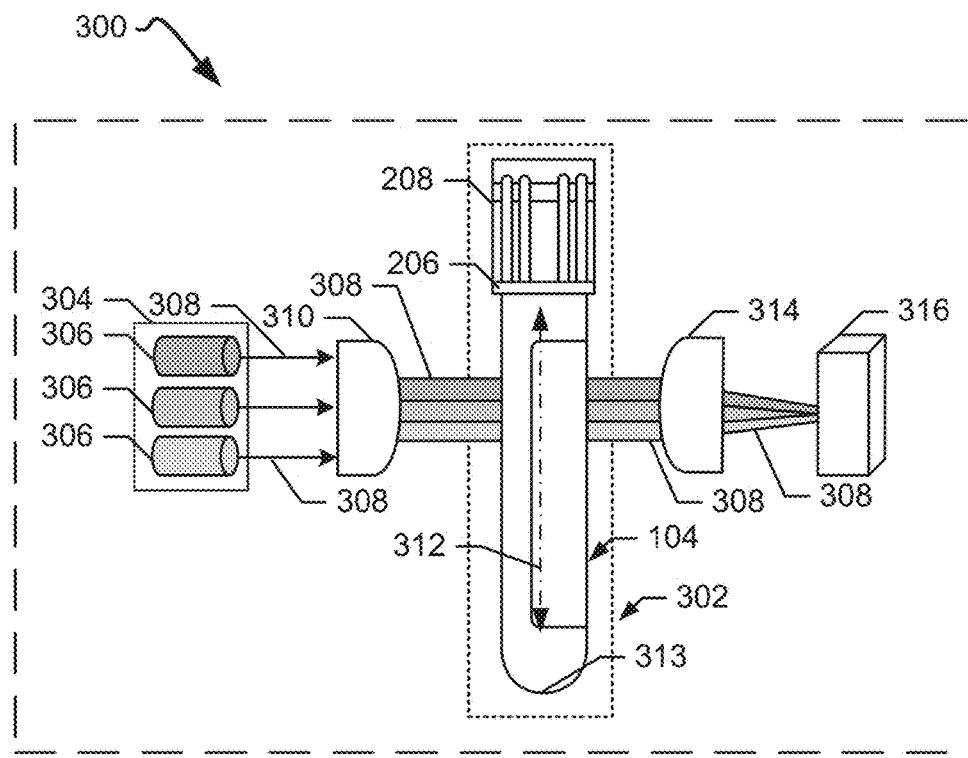
FIG. 3 is a schematic, side view illustration of a first example scanner for use in connection with the example system of FIG. 1, showing a sample container in a first orientation.
Figure 4:
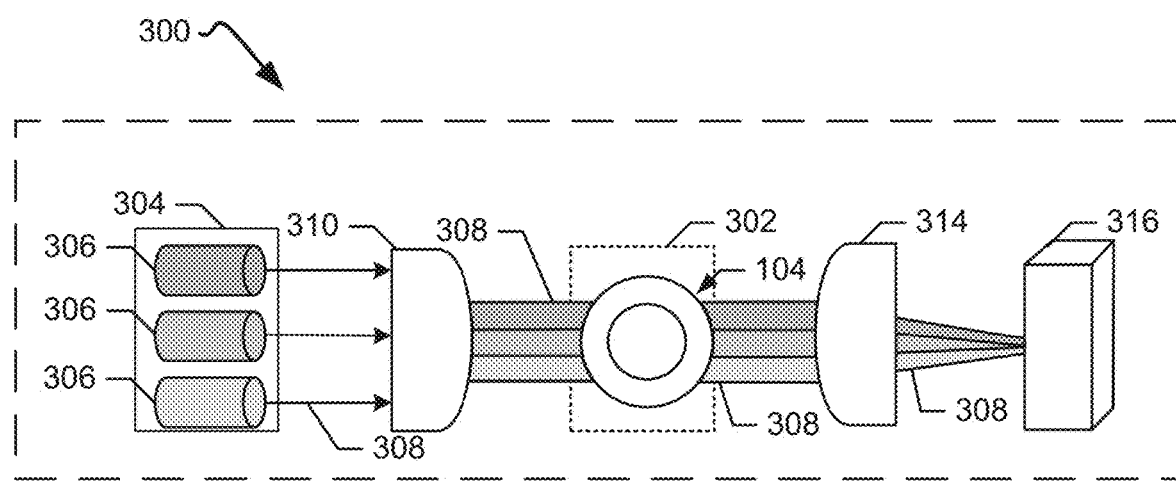
FIG. 4 is a schematic, top view illustration of the example scanner of FIG. 3.

FIG. 3 is a schematic illustration showing a side view of a first example scanner 300 (e.g., the scanner 106 of FIG. 1) for scanning the sample container 104 of FIG. 1 disposed in a sample transporter 302 (e.g., the sample transporter 110 of FIGS. 1 and 2). FIG. 4 is a schematic illustration showing a top view of the first example scanner 300 of FIG. 3. For illustrative purposes, a sample container support (e.g., the sample container support 200 of FIG. 2) and a drive mechanism (e.g., the drive mechanism 204 of FIG. 2) of the sample transporter 302 are not shown in FIGS. 3 and 4.

As illustrated in FIGS. 3 and 4, the example scanner 300 includes a light source 304 (e.g., the light source(s) 112 of FIG. 1). The light source 304 includes one or more light emitters 306. The light emitter(s) 306 emit one or more beams 308 of light. The light emitted by the light emitter(s) 306 via the light beam(s) 308 can include light having different wavelengths (e.g., wavelengths corresponding to red light, green light, or blue light). The example scanner 300 of FIGS. 3 and 4 includes a first lens 310 (e.g., the optics 114 of FIG. 1). The first lens 310 focuses the light beam(s) 308 toward the sample container 104 such that the light beam(s) 308 are transmitted to the sample container 104.

As disclosed above with respect to FIG. 2, the sample transporter 302 moves the sample container 104 along the longitudinal axis of the sample transporter 302 (e.g., via the drive mechanism 204 of FIG. 2), as represented by the arrow 312 in FIG. 3. As such, a path of the light beam(s) 308 intersects the sample container 104 at multiple locations along the longitudinal axis of the sample container 104. In some examples, the sample transporter 302 moves the sample container 104 such that the sample container 104 is exposed to the light beam(s) 308 from a bottom 313 of the sample container 104 to a location corresponding to a height of the sample 102 in the sample container 104 (e.g., as determined by the edge 206 of the sample tube stopper 208). As shown in FIGS. 3 and 4, some or all of the light beam(s) 308 pass through the sample container 104 and exit the sample container 104.

A second lens 314 focuses the light beam(s) 308 that have passed through the sample container 104 and directs the light beam(s) 308 to one or more sensor(s) 316 (e.g., the sensor(s) 116 of FIG. 1). The sensor(s) 316 detect and/or measure the light beam(s) 308 transmitted through, reflected by, or scattered by the sample 102 and/or the sample container 104. As shown in FIGS. 3 and 4, the sensor(s) 316 are disposed on a side of the sample container 104 opposite a side of the sample container 104 that the first light source 304 is disposed.

As disclosed above with respect to FIGS. 1 and 2, the sample container 104 can include one or more labels 202 disposed on an outer surface of the sample container 104. Also, in some examples, the label(s) 202 cover substantially the entire outer surface of the sample container 104. In placing the sample container 104 in the sample transporter 302 of the example scanner 300 of FIG. 3, the user (or robot) does not have to position or align the sample container 104 with respect to the label(s) 202 on the sample container 104 to avoid, for example, the light beam(s) 308 hitting the label(s) 202 as the sample container 104 is moved by the sample transporter 110 during scanning. Rather, in the disclosed examples, the sample container 104 can be positioned in the sample transporter 302 such that the label(s) 202 are in the path of the light emitted from the light source 304 as the sample container 104 is moved along the longitudinal axis by the sample transporter 302. In such examples, as the sample transporter 302 moves the sample container 104 along the longitudinal axis of the sample transporter 302 (e.g., via the drive mechanism 204 of FIG. 2), the light beam(s) 308 emitted by the light source(s) 112 hit the label(s) 202.

Figure 5:
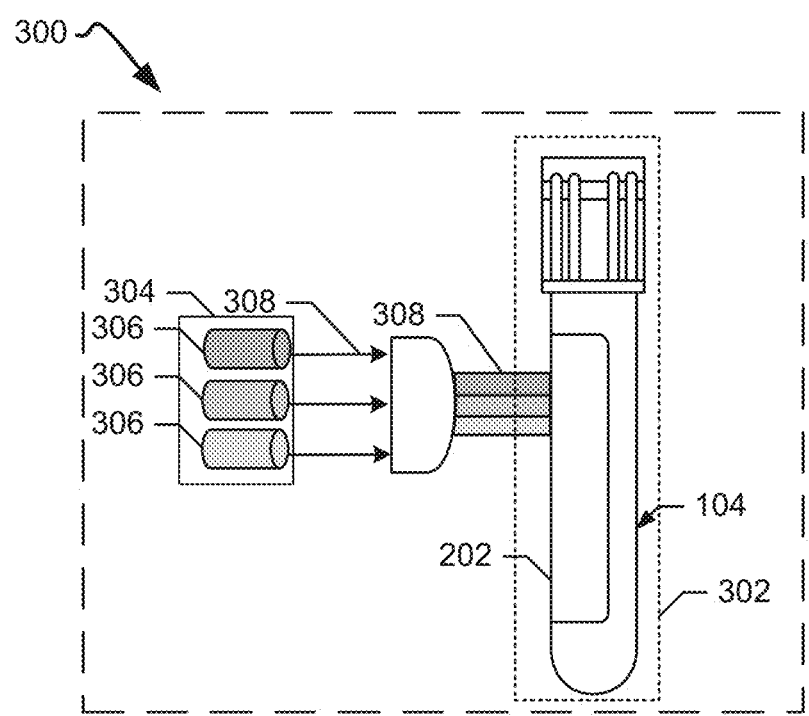
FIG. 5 is a schematic, side view illustration the example scanner of FIG. 3, showing a sample container in a second orientation.

FIG. 5 is a partial view of the example scanner 300 of FIG. 3. As illustrated in FIG. 5, the sample container 104 is disposed in the sample transporter 302 such that the label 202 affixed to an outer surface of the sample container 104 is in a path of the light beam(s) 308 emitted by the light source 304 as the portion of the sample container 104 including the label 202 is moved past the light source 304 via the sample transporter 302. FIGS. 3 and 5 illustrate that a sample container 104 can be disposed in the sample transporter 302 in different orientations regardless of the presence of the label(s) 202. As will be disclosed below, in examples where the label(s) 202 are in the path of the light beam(s) 308, one or more adjustments are applied by the processor 108 of FIG. 1 to the data collected by the sensor(s) 316 to account for the presence of the label(s) 202.

Figure 6:
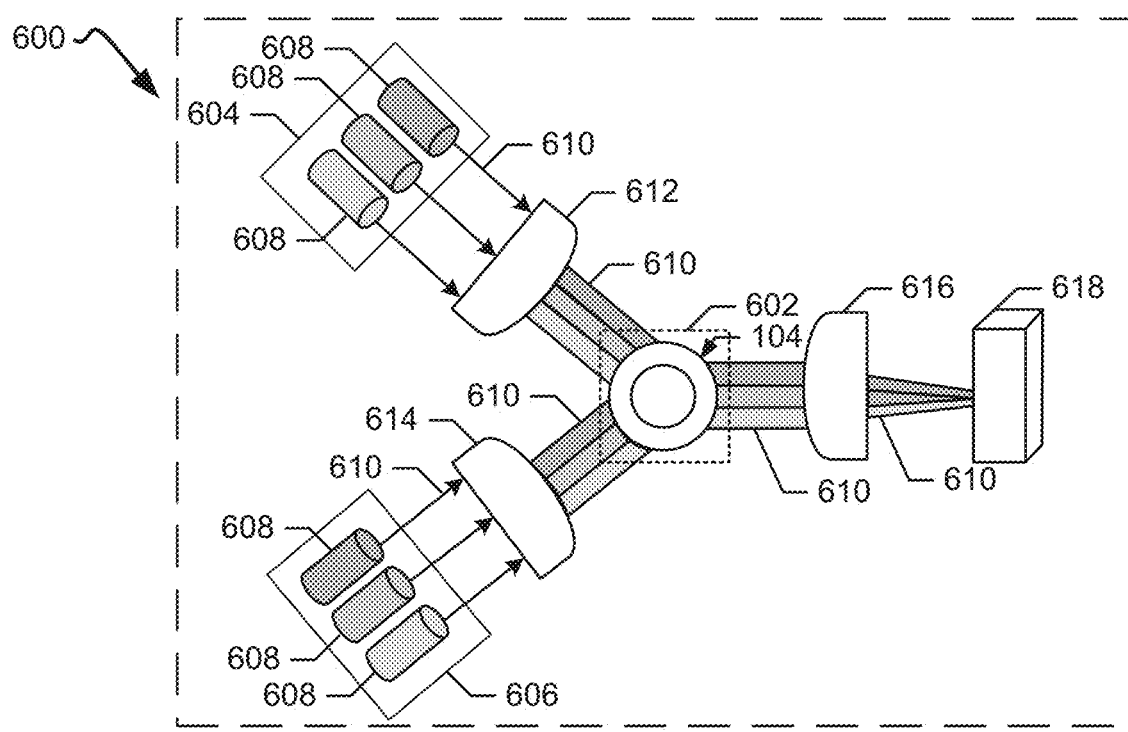
FIG. 6 is a schematic, top view illustration of a second example scanner for use in connection with the example system of FIG. 1.

FIG. 6 is a schematic illustration of a top view of a second example scanner 600 (e.g., the scanner 106 of FIG. 1) for scanning the sample container 104 of FIG. 1 disposed in a sample transporter 602 (e.g., the sample transporter 110 of FIG. 1). For illustrative purposes, a sample container support (e.g., the sample container support 200 of FIG. 2) and a drive mechanism (e.g., the drive mechanism 204 of FIG. 2) of the sample transporter 602 are not shown in FIG. 6.

The second example scanner 600 of FIG. 6 includes a first light source 604 and a second light source 606 (e.g., the light source(s) 112 of FIG. 1). The first and second light sources 604, 606 can be LED arrays or laser arrays. Each of the first and second light sources 604, 606 include light emitters 608 to emit one or more light beams 610. As shown in FIG. 6, the second light source 606 is spaced apart from the first light source 604 about the sample transporter 602. As a result of this arrangement of the first and second light sources 604, 606, the light beams 610 emitted by the respective light emitters 608 of the first and second light sources 604, 606 are transmitted to different portions of the sample container 104 disposed in the sample transporter 602. For example, the light beam(s) 610 emitted from the first light source 604 are transmitted to a first position about a circumference or a perimeter of the sample container 104 and the light beam(s) 610 emitted from the second light source 606 are transmitted to a second position about the circumference or perimeter of the sample container 104.

The example scanner 600 of FIG. 6 also includes a first lens 612 and a second lens 614 (e.g., the optics 114 of FIG. 1). The first lens 612 focuses the light beam(s) 610 emitted from the first light source 604 toward the sample container 104. The second lens 614 focuses the light beam(s) 610 emitted from the second light source 606 toward the sample container 104. Some or all of the light beam(s) 610 emitted from the respective light emitters 608 of the first and second light sources 604, 606 pass through the sample container 104 disposed in the sample transporter 602 at multiple locations as the sample transport 602 moves (e.g., via the drive mechanism 204 of FIG. 2) the sample container 104 along the longitudinal axis of the sample transporter 602. A third lens 616 focuses the light beams 610 that pass through the sample container 104 and directs the light beams 610 to one or more sensors 618 (e.g., the sensor(s) 116 of FIG. 1), which detects or measures the light beams 610 transmitted through, reflected by, or scattered by the sample 102 and/or the sample container 104. As shown in FIG. 6, the sensor(s) 618 are disposed a side of the sample container 104 different from which the first and second light sources 604, 606 are disposed.

In the example of FIG. 6, the arrangement of the light emitters 608, the sensor(s) 618, the lens 612, 614, and the sample transporter 602 form a substantially Y-shape (from the top view). However, the light emitter(s) 608, the sensor(s) 618, the lens 612, 614, and/or the sample transporter 602 can be arranged differently based on, for example, a respective number of light emitter(s) 608, sensor(s) 618, lens 612, 614, etc.; and/or the placement of the light emitter(s) 608, sensor(s) 618, lens 612, 614, etc. relative to the sample transporter 602. For example, the light emitters 608, the sensor(s) 618, the lens 612, 614, and the sample transporter 602 can form a substantially H-shape based on a substantially linear arrangement of the light emitter(s) 608 and the sensor(s) 618. As another example, the sensor(s) 618 and light emitter(s) 608 can be arranged in a substantially circular pattern relative to the sample transporter 602 (e.g., three light emitter(s) 608 distributed at an angle relative to the sample container 104 and three sensor(s) 618 distributed at an angle relative to the sample container 104). The arrangement of any of the light emitters, lens, and/or sensors of FIGS. 3-6 can differ from the illustrated examples.

In some examples, the example scanner 600 of FIG. 6 is used to detect cloudiness or turbidity of the sample. A cloudy sample can result in the scattering of light within the sample 102 or reflection of the light off of particles in the cloudy sample. A dual emitter array in the form of the first and second light sources 604, 606 arranged about the sample container 104 can be used to detect cloudiness in the sample 102.

Figure 7:
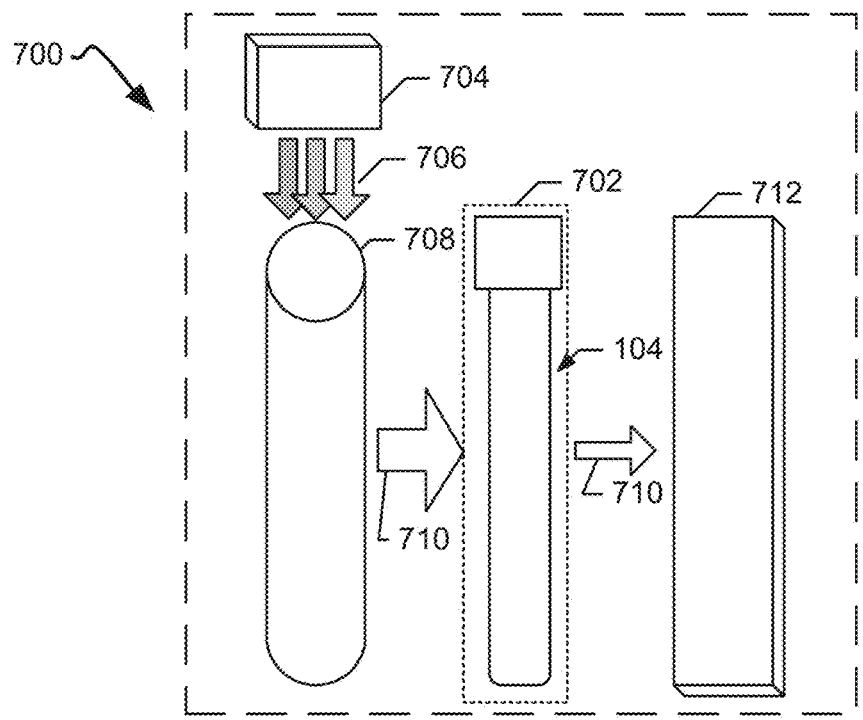
FIG. 7 is a schematic, side view illustration of a third example scanner for use in connection with the example system of FIG. 1.

FIG. 7 is a schematic illustration of a side view of a third example scanner 700 (e.g., the scanner 106 of FIG. 1) for scanning the sample container 104 of FIG. 1 disposed in a sample transport 702 (e.g., the sample transporter 110 of FIG. 1). For illustrative purposes, a sample container support (e.g., the sample container support 200 of FIG. 2) and a drive mechanism (e.g., the drive mechanism 204 of FIG. 2) of the sample transport 702 are not shown in FIG. 7.

The example scanner 700 of FIG. 7 includes a light source 704 (e.g., the light source(s) 112 of FIG. 1). For example, the light source 704 of FIG. 7 can be an LED emitter array that emits one or more beam(s) of light, or first light beam(s) 706, including light having different wavelengths corresponding to red light, green light, and/or blue light. The example scanner 700 of FIG. 7 includes a light pipe 708. The first light beam(s) 706 emitted by the light source 704 are emitted into the light pipe 708. The first light beam(s) 706 are reflected within the light pipe 708 and emitted by the light pipe 708 as a second light beam 710. The second light beam 710 has a substantially uniform color. The second light beam 710 is emitted from the light pipe 708 in a direction substantially perpendicular to the sample container 104. The second light beam 710 passes through the sample container 104 disposed in the sample transport 702 at multiple locations as the sample transport 702 moves (e.g., via the drive mechanism 204 of FIG. 2) the sample container 104 along the longitudinal axis of the sample transport 702.

The example scanner 700 of FIG. 7 includes one or more sensors 712 (e.g., the sensor(s) 116 of FIG. 1). The sensor(s) 712 can be disposed on a sensor board. The second light beam 710 is directed to the sensor(s) 712 after passing through the sample container 104. The sensor(s) 712 of the example scanner 700 of FIG. 7 detect or measure the second light beam 710 transmitted through, reflected by, or scattered by the sample 102 and/or the sample container 104.

Figure 8:
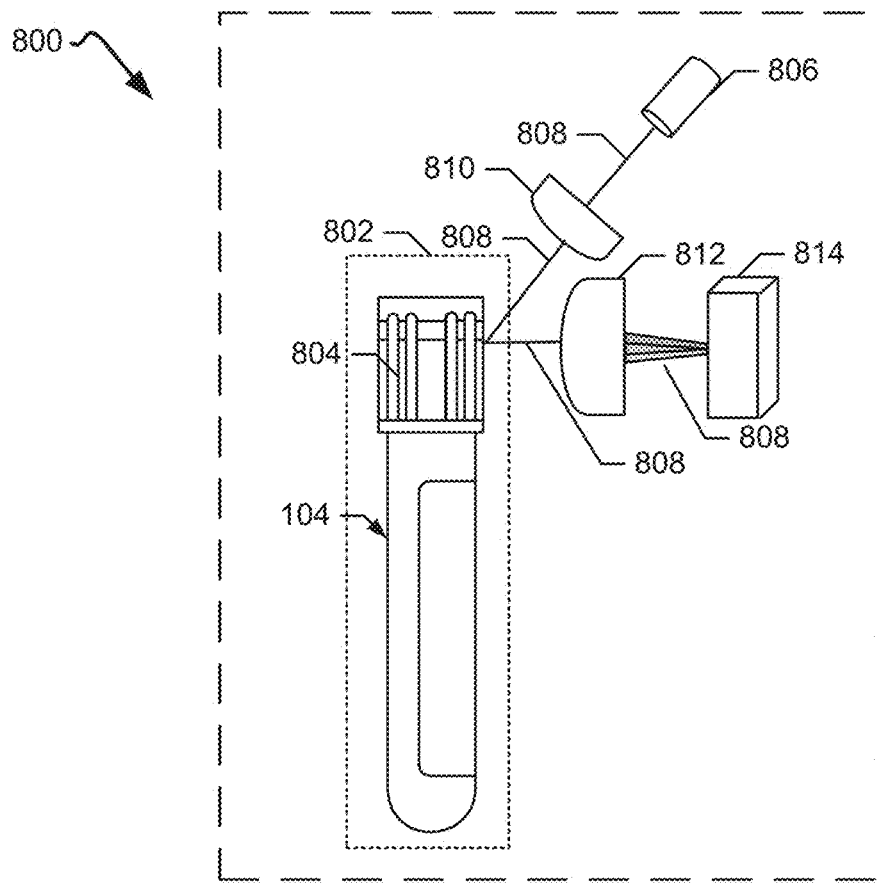
FIG. 8 is a schematic, side view illustration of a fourth example scanner for use in the connection with the example system of FIG. 1.

FIG. 8 is a schematic illustration of a side view of a fourth example scanner 800 (e.g., the scanner 106 of FIG. 1) for scanning the sample container 104 of FIG. 1 disposed in a sample transporter 802 (e.g., the sample transporter 110 of FIGS. 1 and 2). For illustrative purposes, a sample container support (e.g., the sample container support 200 of FIG. 2) and a drive mechanism (e.g., the drive mechanism 204 of FIG. 2) of the sample transport 802 are not shown in FIG. 8. The example scanner 800 of FIG. 8 can be used to determine a color of a cap 804 disposed on the sample container 104. The example scanner 800 can also be used to determine a color of a stopper, or a plug having a portion disposed inside the sample container 104 (e.g., the sample tube stopper 208). Also, in some examples, the scanner 800 of FIG. 8 is implemented with the first example scanner 300 of FIGS. 3-5, the second example scanner 600 of FIG. 6, or the third example scanner 700 of FIG. 7, to scan the sample container 104 and the cap 804 of the sample container 104.

The example scanner 800 includes a light source 806 (e.g., the light source(s) 112 of FIG. 1), which emits one or more light beams 808. In some example, the light source 806 is an LED emitting white light, full spectrum white light, or an RGB array. As illustrated in FIG. 8, a first lens 810 (e.g., the optics 114 of FIG. 1) directs the light beam(s) 808 emitted by the light source 806 such that the light beam(s) 808 are transmitted to the cap 804 of the sample container 104. Some or all of the light beam(s) 808 bounce off of or are reflected by the cap 804 and are received by a second lens 812. The second lens 812 directs the light beam(s) 808 to one or more sensors 814 (e.g., the sensor(s) 116 of FIG. 1), which detects or measures the light beam(s) 808 reflected by the cap 804. As shown in FIG. 8, because the light beams(s) 808 do not pass through the sample container 104, the light source 806 and the sensor(s) 814 are disposed on substantially a same side of the sample container 104 such that the second lens 812 is in a path of the light beam(s) 808 that bounce off of or are reflected the cap 804.

As shown in FIGS. 3-8, the example scanner 106 of FIG. 1 including the sample transporter 110, the light source(s) 112, the optics 114, and the sensor(s) 116 can have different arrangements. For example, the scanner 106 can include one or more light sources 112, including two light sources 604, 606 as shown in the second example scanner 600 of FIG. 6 or any other number of light sources. In some examples, each light source is associated with a lens or optics 114. In other examples, there are fewer optics 114 than light sources 112 or no optics 114. Also, the positioning of the light source(s) 112, the optics 114, and/or the sensor(s) relative to the sample transporter 110 and/or the sample container 104 can vary. For example, the light source(s) 112 and the sensor(s) 116 can be located on opposite sides of the sample container 104 or on substantially the same side of the sample container 104. The number of light source(s) 112 and/or the positioning of the light source(s) 112 can be customized based on properties of interest of the sample 102 and/or the sample container 104, such as sample turbidity and cap or stopper color. Additionally, the positioning of the sample container 104 in the sample transporter 110 relative to the light source(s) 112 can be varied irrespective of one or more label(s) 202 affixed to the sample container 104, as illustrated in FIGS. 3 and 5.

Figure 9:
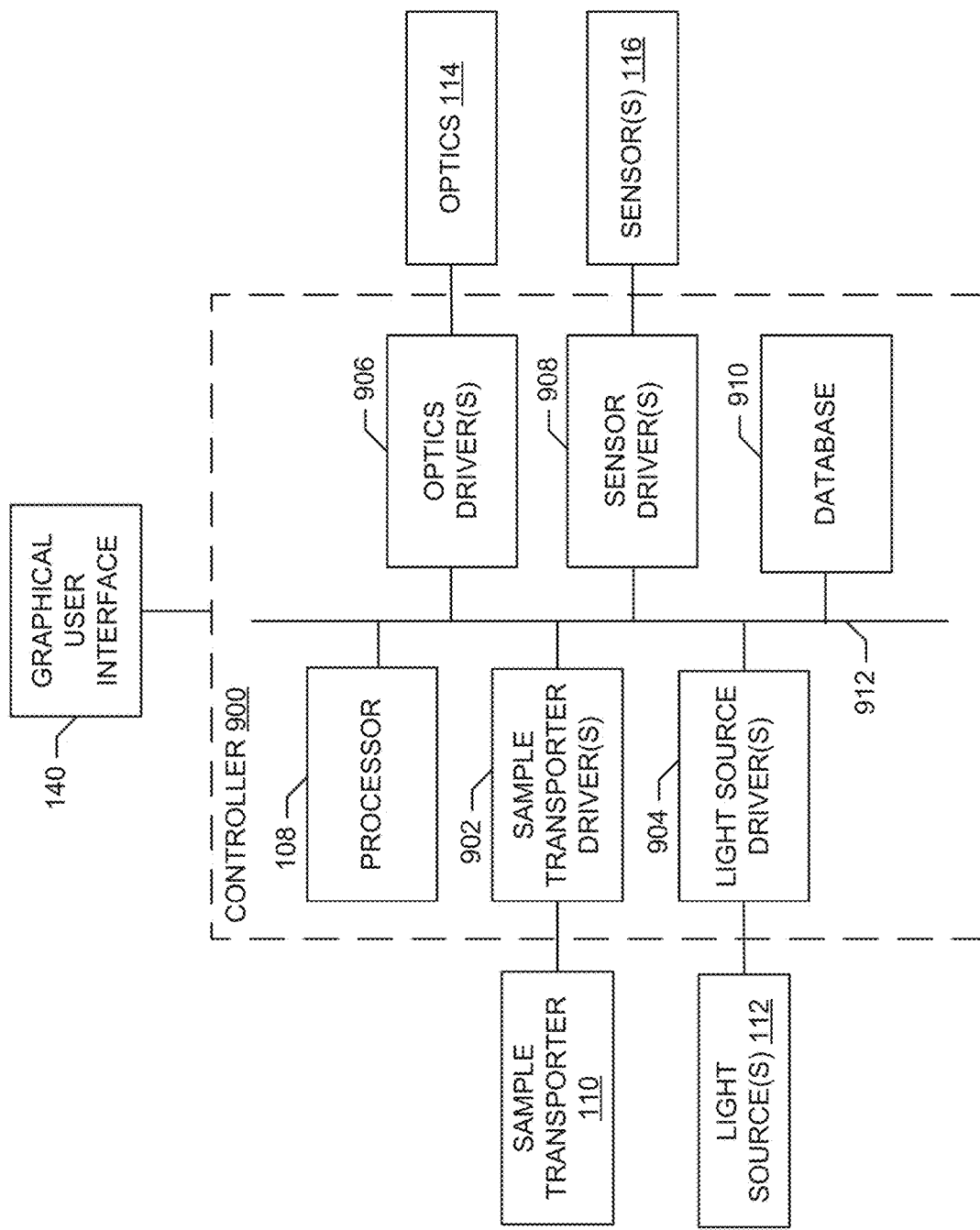
FIG. 9 is a block diagram of an example processing system for scanning a sample that can be used to implement the examples disclosed herein.

FIG. 9 is a block diagram providing further details of the example system 100 of FIG. 1 for scanning a sample container (e.g., the sample container 104 of FIGS. 1-8) containing a sample (e.g., the sample 102 of FIGS. 1-8). Specifically, FIG. 9 provides details of an example controller 900 for controlling a scanner for scanning the sample container.

The example controller 900 includes a sample transporter driver 902. In some examples, the example processing system 900 includes one or more sample transporter driver(s) 902. The sample transporter driver(s) 902 are communicatively coupled to the sample transporter 110 of FIG. 1. The sample transporter driver(s) 902 control operation of the sample transporter 110, including, for example, a drive mechanism of the sample transporter 110 (e.g., the drive mechanism 204 of FIG. 2). For example, the sample transporter driver(s) 902 control a speed at which the sample transporter 110 moves a sample container disposed in the sample transporter 110 (e.g., via the drive mechanisms 204 of FIG. 2) along a longitudinal axis of the sample transporter 110. The sample transporter driver(s) 902 control a number of times the sample transporter 110 moves the sample container relative to a reference point of the sample transporter 110 (e.g., a starting position for loading the sample container in the sample transporter 110). In some examples, the sample transporter driver(s) 902 detect a size of a sample container, a weight of the sample container, and/or a presence of a stopper on the sample container to determine a distance over which the sample transporter 110 moves the sample container based on, for example, a sample liquid level in the sample container. Also, a processor associated with the controller 900, such as the example processor 108 of FIG. 1, operates the sample transporter driver(s) 902 and, thus, the sample transporter 110 in accordance with a sample container transport protocol.

The example controller 900 includes one or more light source driver(s) 904. The light source driver(s) 904 are communicatively coupled to the one or more light source(s) 112 of FIG. 1. The light source driver(s) 904 control emission of light (e.g., the light beam(s) 308, 610, 706, 710, 808 of FIGS. 3-8) from the light source(s) 112 (e.g., via the light emitter(s) 306, 608 of FIGS. 3-5, 6). For example, the light source driver(s) 904 control the duration of emission of light by the light source(s) 112, wavelength(s) of the light emitted by the light source(s) 112 (e.g., corresponding to red, green, and/or blue light), and/or an intensity of the light emitted by the light source(s)). The example processor 108 operates the light source driver(s) 904 and, thus, the light source(s) 112 in accordance with a light emission protocol.

The example controller 900 includes one or more optics driver(s) 906. The optics driver(s) 906 are communicatively coupled to the optics 114 of FIG. 1. The optics 114 can be, for example, one or more lens or a light pipe. The optics 114 focus the light emitted from the light source(s) 112. The optics driver(s) 906 control a position of the optics 114 with respect to, for example, an angle of the optics 114 to focus or direct the light emitted by the light source(s) 112 to the sample container disposed in the sample transporter 110. The optics driver(s) 906 also control a position of the optics 114 with respect to an angle of the optics 114 to focus or direct the light transmitted through the sample container to one or more sensor(s). Also, the example processor 108 operates the optics driver(s) 906 and, thus, the optics 114 in accordance with an optics positioning protocol.

The example controller 900 also includes one or more sensor driver(s) 908. The sensor driver(s) are communicatively coupled to one or more sensors 116. The sensor driver(s) 908 control the detection of light transmitted through the sample container in the sample transporter 110 from the light source(s) 112 by the sensor(s) 116. For example, the sensor driver(s) 908 control the wavelengths of light detected by the sensor(s) 116 based on, for example, the wavelengths of light emitted by the light source(s) 112, the collection of signals by the sensor(s) 116, the output of the signals as digital data, and the storage of the data. The sensor driver(s) 908 also control, for example, calibration of the sensor(s) 116, the resolution of the sensor(s) 116, and the detection of noise by the sensor(s) 116. Also, the example processor 108 operates the sensor driver(s) 908 and, thus, the sensor(s) 116 in accordance with a light detection protocol.

The example controller 900 also includes a database 910 that stores information related to the operation of the example system 100 of FIG. 1. In some examples, the database 910 is the example database 126 of FIG. 1. In other examples, the database 910 is a different database than the database 126 of FIG. 1. The information may include, for example, information about the wavelengths of light emitted by the light source(s) 112, the amount of light detected by the sensor(s) 116, and locations of the sample container exposed to the light source(s) 112 during scanning of the sample containers and corresponding to measurements collected by the sensor(s) 116, etc. The database 910 can also store information such as the size of the sample container disposed in the sample transporter 110.

The example controller 900 is associated with a graphical user interface such as, for example, the graphical user interface 140 of FIG. 1. An operator or technician interacts with the controller 900 and, thus, the example system 100, via the interface 140 to provide, for example, commands related to operation of the sample transporter 110, such as the number of scans of the sample container to be conducted, which controls the number of times the sample transporter 110 moves the sample container to and from a reference point along the longitudinal axis of the sample transporter 110, the wavelengths of the light to be emitted by the light source(s) 112, and the duration of emission of light by the light source(s) 112. The interface 140 may also be used by the operator to obtain information related to the detection of light by the sensor(s) 116, the status of any scans completed and/or in progress, check parameters such as positioning of the sample container in the sample transporter 110, and/or to perform calibrations.

In the example shown, the processing system components 902, 904, 906, 908, 910 are communicatively coupled to other components of the example controller 900 via communication links 912. The communication links 912 may be any type of wired connection (e.g., a databus, a USB connection, etc.) and/or any type of wireless communication (e.g., radio frequency, infrared, etc.) using any past, present or future communication protocol (e.g., Bluetooth, USB 2.0, USB 3.0, etc.). Also, the components of the example controller 900 may be integrated in one device or distributed over two or more devices.

While an example manner of implementing the example system 100 of FIG. 1 is illustrated in FIGS. 1-9, one or more of the elements, processes and/or devices illustrated in FIGS. 1 and 9 may be combined, divided, re-arranged, omitted, eliminated and/or implemented in any other way. Further, the example scanner 106, the example processor 108, the example sample transporter 110, the example light source(s) 112, the example sensor(s) 116, the example optics 114, the example data analyzer 120, the example label detector 122, the example luminance restorer 124, the example database(s) 126, 910, the example HIL analyzer 130, the example sample layer analyzer 132, the example sample volume analyzer 134, the example container analyzer 136, the example quality evaluator 138, the example controller 900, the example sample transporter driver(s) 902, the example light source driver(s) 904, the example optics driver(s) 906, the example sensor driver(s) 908, and/or, more generally, the example system 100 of FIGS. 1 and 9 may be implemented by hardware, software, firmware and/or any combination of hardware, software and/or firmware. Thus, for example, any of the example scanner 106, the example processor 108, the example sample transporter 110, the example light source(s) 112, the example sensor(s) 116, the example optics 114, the example data analyzer 120, the example label detector 122, the example luminance restorer 124, the example database(s) 126, 910, the example HIL analyzer 130, the example sample layer analyzer 132, the example sample volume analyzer 134, the example container analyzer 136, the example quality evaluator 138, the example controller 900, the example sample transporter driver(s) 902, the example light source driver(s) 904, the example optics driver(s) 906, the example sensor driver(s) 908, and/or, more generally, the example system 100 of FIGS. 1 and 9 could be implemented by one or more analog or digital circuit(s), logic circuits, programmable processor(s), application specific integrated circuit(s) (ASIC(s)), programmable logic device(s) (PLD(s)) and/or field programmable logic device(s) (FPLD(s)). When reading any of the apparatus or system claims of this patent to cover a purely software and/or firmware implementation, at least one of the example scanner 106, the example processor 108, the example sample transporter 110, the example light source(s) 112, the example sensor(s) 116, the example optics 114, the example data analyzer 120, the example label detector 122, the example luminance restorer 124, the example database(s) 126, 910, the example HIL analyzer 130, the example sample layer analyzer 132, the example sample volume analyzer 134, the example container analyzer 136, the example quality evaluator 138, the example controller 900, the example sample transporter driver(s) 902, the example light source driver(s) 904, the example optics driver(s) 906, the example sensor driver(s) 908, and/or, more generally, the example system 100 of FIGS. 1 and 9 is/are hereby expressly defined to include a tangible computer readable storage device or storage disk such as a memory, a digital versatile disk (DVD), a compact disk (CD), a Blu-ray disk, etc. storing the software and/or firmware. Further still, the example system 100 of FIGS. 1-9 may include one or more elements, processes and/or devices in addition to, or instead of, those illustrated in FIGS. 1-9, and/or may include more than one of any or all of the illustrated elements, processes and devices.

Referring again to FIG. 1, the readings collected by the sensor(s) 116 during scanning of the sample container 104 are transmitted to the processor 108 for data processing and analysis. Signal data from the sensor(s) 116 is processed by the data analyzer 120 of FIG. 1. The signal data can include data collected by the sensor(s) 116 with respect to red, green, and/or blue color channels. The signal data can also include data for a clear channel, or a combination of the red, green, and blue colors. The clear channel provides for a measure of luminance, or an intensity of the light. In other examples, the signal data is an infrared signal. In some examples, the readings collected by the sensor(s) 116 are converted from an analog signal to a digital signal by an analog-digital converter associated with the processor 108. The digital signal data can include, for example, color counts for clear, red, green, and blue channels.

In some examples, the scanner 106 scans the sample container 104 one or more times. For example, the scanner 106 can scan the sample container 104 along a length of the sample container from the bottom of the sample container 104 to the top of the sample container 104, as disclosed in connection with FIG. 2. Based on signal data generated during the scanning of the length of the sample container 104, the data analyzer 120 determines locations of areas of interest such as the location of the stopper 208 coupled to the sample container 104, the layers of the sample (e.g., plasma, white blood cells, red blood cells), and the bottom 313 of the sample container 104. The scan of the length of the sample container 104 can also be used to detect the presence of one or more labels on the sample container 104, as will be disclosed below. After locations of the sample container 104 are determined, the sample transporter 110 can move the sample container 104 to an area of interest for scanning, such as for scanning of the stopper 208 of the sample container 104 to verify color of the stopper 208. As another example, the sample transporter 110 can move the sample container 104 to an area where the sample 102 is disposed in the sample container 104 for analysis of light absorption properties of the sample 102 for a HIL analysis based on sample color.

Figure 10:
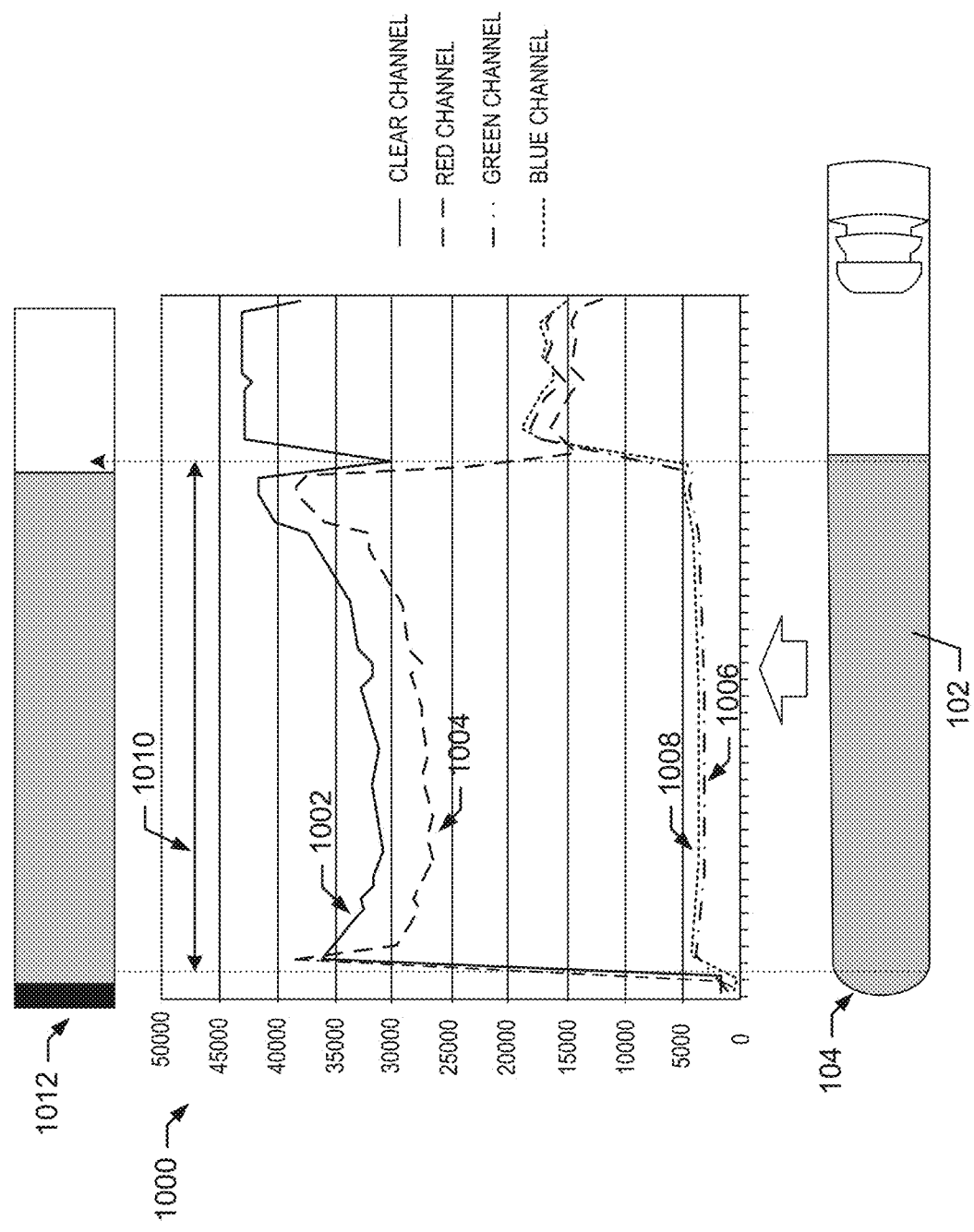
FIG. 10 is a diagram illustrating an analysis of example signal data collected from scanning a sample container using the example system of FIG. 1, where the sample container does not have a label affixed thereto.

FIG. 10 is an example diagram illustrating an analysis of signal data by the data analyzer 120 collected during scanning of the sample container 104 including the sample 102 disposed therein with the scanner 106 of the example system 100 of FIG. 1. The example signal data of FIG. 10 was collected from a sample container 104 did not have any labels affixed to an outer surface thereof. As shown in FIG. 10, a portion of the sample container 104 contains the sample 102. During one or more scans, readings of the light emitted through the sample container 104 are collected at multiple locations along the sample container 104. The data collected includes wavelengths corresponding to, for example, red, green, blue, and clear channels, as graphically represented in graph 1000 of FIG. 10. For example, the graph 1000 includes clear signal data 1002, red signal data 1004, green signal data 1006, and blue signal data 1008. In the example graph 1000, the y-axis values are color counts for the respective color signal data 1002, 1004, 1006, 1008. In other examples, infrared signal data is collected by the sensor(s) 116.

The graph 1000 of FIG. 10 shows the signal data 1002, 1004, 1006, 1008 collected at multiple locations of the sample container 104, including the locations where the sample 102 is disposed in the sample container 104, as represented by the arrowed line 1010. The data analyzer 120 generates a digital sample representation 1012 based on the clear, red, green, and blue signal data 1002, 1004, 1006, 1008. The sample representation 1012 is a representation of the characteristics of the sample 102 and/or the sample container 104 based on measurements of the light passing through the sample container 104 of the signal data 1002, 1004, 1006, 1008 (e.g., as represented by the color counts of the example graph 1000 of FIG. 10). For example, the sample representation 1012 is a representation of the color of the sample 102 based on the signal data collected during scanning of the sample 102. For example, if the sample 102 is a blood sample, the red signal data 1004 represents the dominant color detected during the scanning of the sample 102. Thus, the signal representation 1012 reflects the red color of the sample 102.

In generating the representation of the color of the sample 102, the data analyzer 120 accounts for luminance, or a brightness of the light passing through the sample 102. The data analyzer 120 applies a luminance value as a percentage ($Luminance_{Percentage}$) to each of the red, green, and blue signal data 1004, 1006, 1008 ($RGB_{Value}$), for example, using the algorithm $RGB_{Value} * Luminance_{Percentage}$. The luminance percentage is based on an output of one or more light sources (e.g., the light source(s) 112 of FIG. 1). As an example, during scanning of the sample container 104, the sample container 104 passes by an LED emitter. A degree to which the LED emitter is turned on to emit light (e.g., similar to a dimmer switch) determines the luminance percentage. In other examples, the sample container 104 passes by an array of RGB sensors with corresponding LED emitters. In such examples, the luminance percentage is determined based on a combination of luminance for the RGB sensors. For example, each of the RGB sensors can be flashed at substantially the same percentage with respect to an emittance of light.

In accounting for luminance, the data analyzer 120 accounts for variability in the brightness of light passing through the sample container 104 and avoids saturation of color, or a loss of resolution in the sample representation 1012 for color signal data above a threshold color count. As a result, the data analyzer 120 more completely detects color variations in the sample 102 (e.g., variations of the color red) as compared to generating a sample representation based on the $RGB_{Value}$ alone at each scanned location along the sample container 104. The increased resolution of the sample representation 1012 as compared to generating a sample representation without accounting for luminance provides for increased accuracy in analyzing the quality of the sample using, for example, the HIL analyzer 130 of the processor 108.

As disclosed above with respect to FIGS. 2-7, in some examples, the sample container 104 has one or more labels 202 affixed to the outer surface of the sample container 104 and the labels are in a path of the light emitted by the light source(s) 112 during scanning of the sample container 104. In some examples, a qualitative analysis of the sample container 104 and/or the sample 102 (e.g., a HIL analysis) can be performed based on data collected from scanning the sample container 104 below and/or above the one or more labels 202. However, in some examples, a substantial portion of the sample container 104 is covered with the one or more labels 202. For example, substantially an entire length of the sample container 104 can be covered with one or more labels 202. When the sample container 104 having a substantial portion covered by the label(s) 202 is scanned by the scanner 106, the signal data collected during the scanning is partially or substantially attenuated as a result of the absorption of light by the label(s) 202. In such examples, the signal data collected from the scan of the sample container 104 can be restored to generate data that can be used to assess the quality of the sample container 104 and/or the sample 102 disposed therein.

Figure 11:
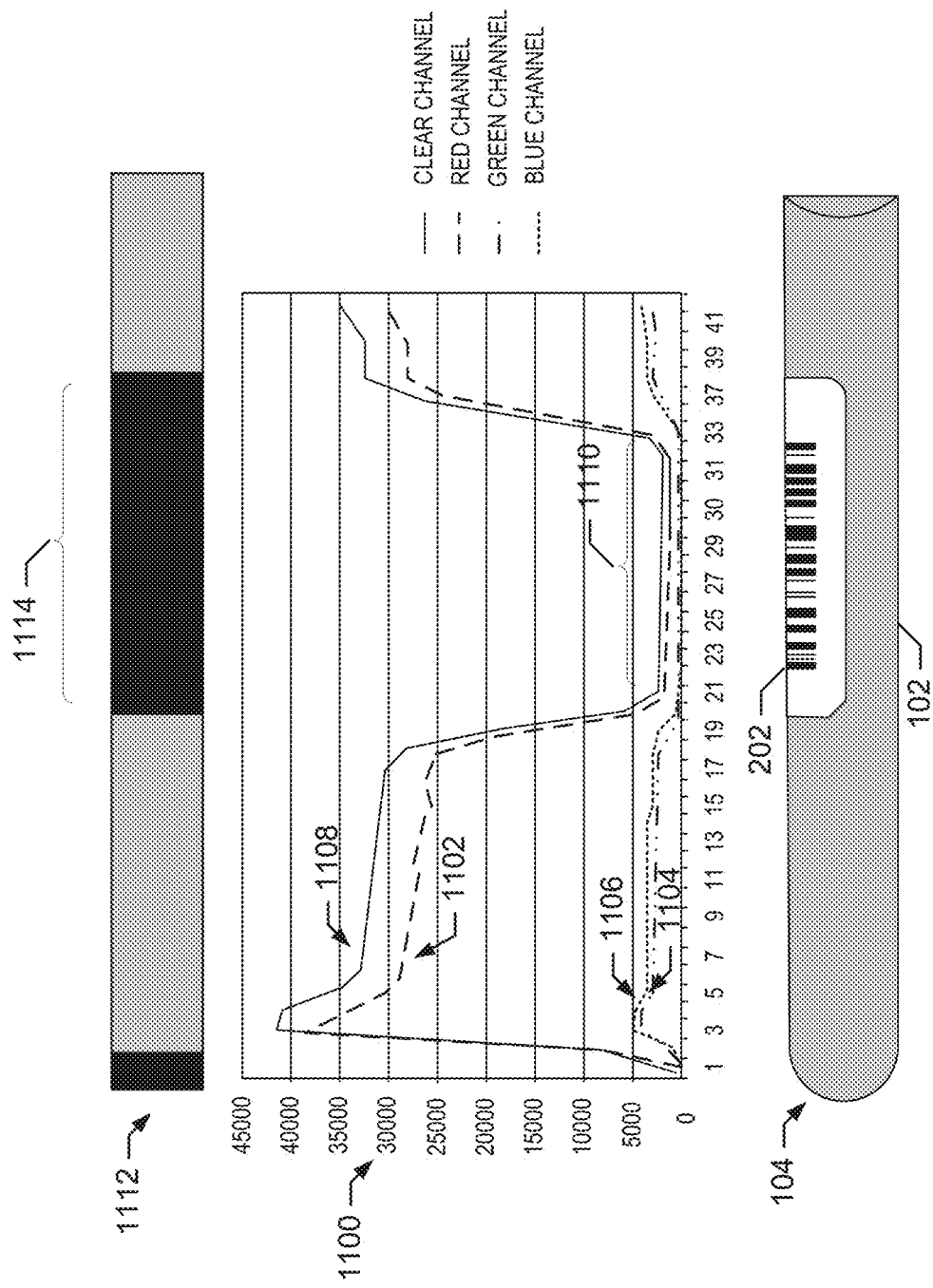
FIG. 11 is a diagram illustrating an analysis of example signal data collected from scanning a sample container using the example system of FIG. 1, where the sample container has one or more labels affixed thereto.

FIG. 11 is an example diagram showing an analysis of signal data by the data analyzer 120, where the signal data is collected from the sample container 104 with a label 202 affixed to a surface of the sample container 104. In some examples, the sample container 104 has two or more labels 202 affixed to the surface of the sample container 104. Also, in some examples, the label(s) 202 cover a substantially portion of the surface of the sample container 104 (e.g., the label(s) 202 substantially cover the length of the sample container 104).

During scanning of the sample container 104 with the label 202, the sensor(s) 116 collect red signal data 1102, green signal data 1104, blue signal data 1106, and clear signal data 1108 as the scanner 106 scans the sample container 104 (e.g. one or more scans). In other examples, the sensor(s) 116 collect infrared signal data. The light from the light source(s) 112 hits the label 202 during scanning. As shown in an example graph 1100 of FIG. 11, the presence of the label 202 causes an attenuation of the red, green, blue, and clear signal data 1102, 1104, 1106, 1108 due to the absorbance of light by the label 202 and, thus, loss of the signal data 1102, 1104, 1106, 1108. For example, each of red, green, blue, and clear signal data 1102, 1104, 1106, 1108 includes an attenuated portion 1110. Thus, when the data analyzer 120 generates a digital sample representation 1112 based on the signal data 1102, 1104, 1106, 1108, the sample representation 1112 includes an interrupted portion 1114 corresponding to the location of the label 202 on the sample container 104 and the attenuation of the signal data 1102, 1104, 1106, 1108 at that location. For example, the attenuated portions can cause the interrupted portion 1114 to appear as a shadow in the sample representation 1112.

As illustrated in FIG. 11, the presence of the label 202 causes an incomplete representation of the sample 102 in the sample representation 1112 as a result of the interrupted portion 1114. In examples where the label 202 covers a substantial portion the sample container 104 (e.g., substantially the entire length of the sample container 104), a substantial portion (e.g., substantially all) of the sample representation 1112 can include the interrupted portion 1114. The incomplete representation of the sample affects the determination of the quality of the sample by the processor 108. To account for the presence of the one or more labels 202 on the sample container 104, the label detector 122 and the luminance restorer 124 of the processor 108 restore the attenuated signal data caused by the label(s) 202. In some examples, the processor 108 analyzes a sample representation including the restored data to determine the quality of the sample 102.

The example label detector 122 of the processor 108 of FIG. 1 detects the presence of the one or more labels 202 on the sample container 104 based on attenuation of the signal data 1102, 1104, 1106, 1108 due to absorbance, such as the attenuated portion 1110 of the clear signal data 1108 of FIG. 11. For example, the label detector 122 determines that the label 202 is on the sample container 104 if each of the red signal data 1102, the green signal data 1104, the blue signal data 1106, and the clear signal data 1108 include portions that attenuate below a predetermined threshold for each color signal based on, for example, color counts or wavelengths. In some examples, the threshold is based on signal data from locations on the sample container 104 (or another sample container 104 for calibration purposes) that do not include the label 202 or signal data collected without a sample container (e.g., light passing through air). For example, signal data collected from locations on the sample container 104 that do not include the label 202 can be used as baseline data. The label detector 122 detects the presence of the label 202 if signal data collected from other locations of the sample container 104 falls below the baseline data threshold. In other examples, the label detector 122 detects the presence of the label 202 based on an analysis of signal data collected from scanning the sample container 104 with infrared light to detect absorbance or signal loss due to the label 202.

In some examples, the label detector 122 detects a number and/or thickness of the label(s) 202 on the sample container 104. For example, the number of label(s) 202 can be determined based on an amount of absorbance or loss of signal data as compared to, for example, signal data collected from sample containers having a known number of label(s) 202. If the label detector 122 determines that there are one or more labels 202 on the sample container 104, the luminance restorer 124 determines a respective signal restoration coefficient or adjustment factor to be applied to the signal data 1102, 1104, 1106, 1108 to account for the presence of the one or more labels 202. To determine the signal restoration coefficient to be applied to, for example the attenuated portion 1110 of the clear signal data 1108, the luminance restorer 124 retrieves the coefficient from the coefficient table 128 of the database 126 of the processor 108 of FIG. 1.

As another example, if the label 202 covers substantially an entire length of the sample container 104, the signal data collected from scanning the sample container 104 includes substantially all attenuated data, rather than a combination of signal data corresponding to locations on the sample container 104 that do not contain the label 202 and attenuated signal data corresponding to portions of the sample container 104 that contain the label 202. In such examples, because the attenuated signal data corresponds to substantially the entire length of the sample container 104, the signal data may not contain baseline data (e.g., data corresponding to portions of the sample container 104 without the label 202) to use for detection of the label 202. In such examples, a thickness of the label 202 can be determined based on the amount of absorbance or loss of signal data (e.g., as detected by scanning the sample container with infrared light) as compared to, for example, signal data collected from sample containers having a label 202 with a known thickness. The luminance restorer 124 determines a respective signal restoration coefficient or adjustment factor from the coefficient table 128 to be applied to the signal data 1102, 1104, 1106, 1108 to account for the label 202 extending along a substantial length of the sample container 104 based on label thickness.

Figure 12:
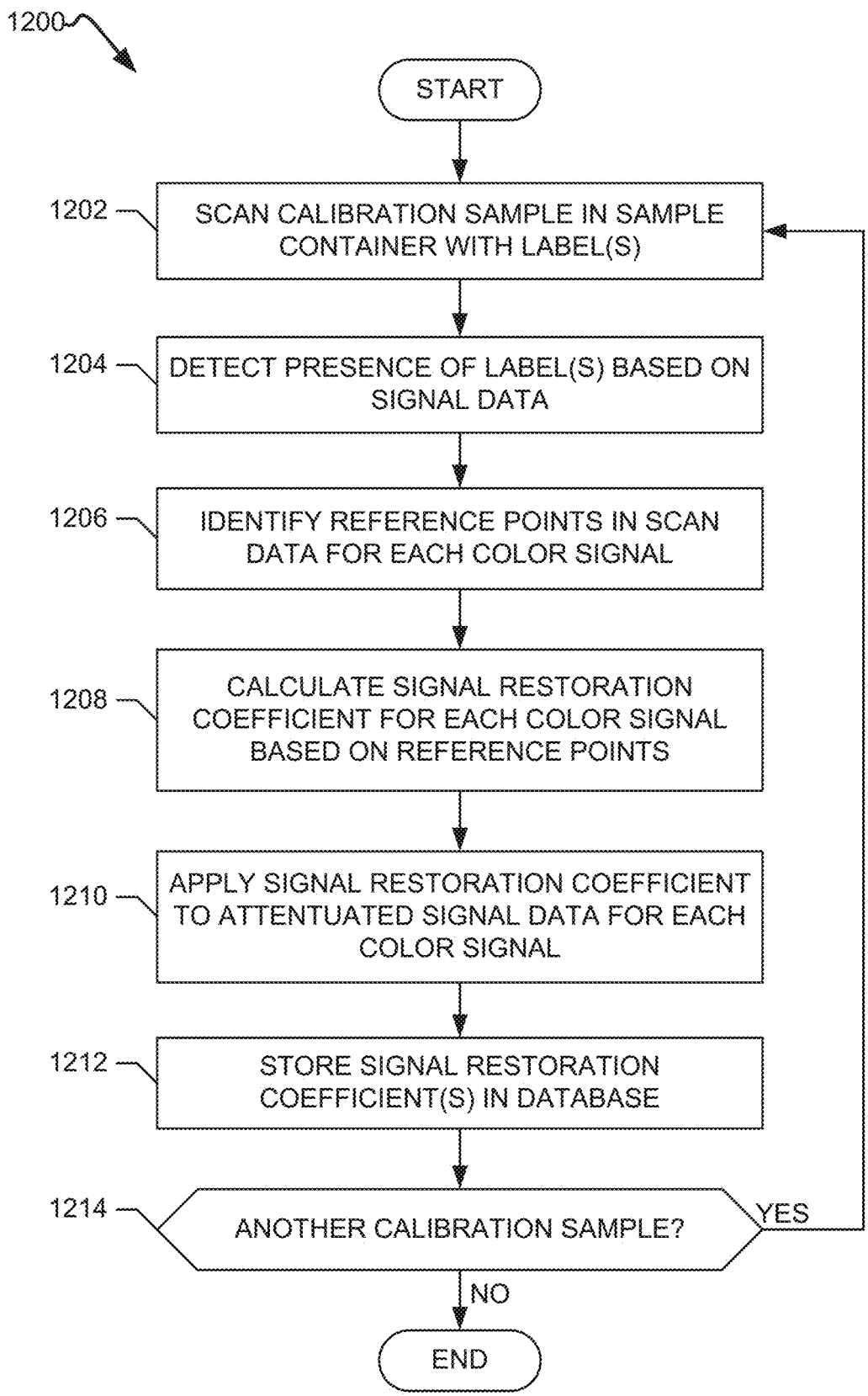
FIG. 12 is a flow diagram of an example method for determining a signal restoration coefficient that can be used to implement the examples disclosed herein.
Figure 13A:
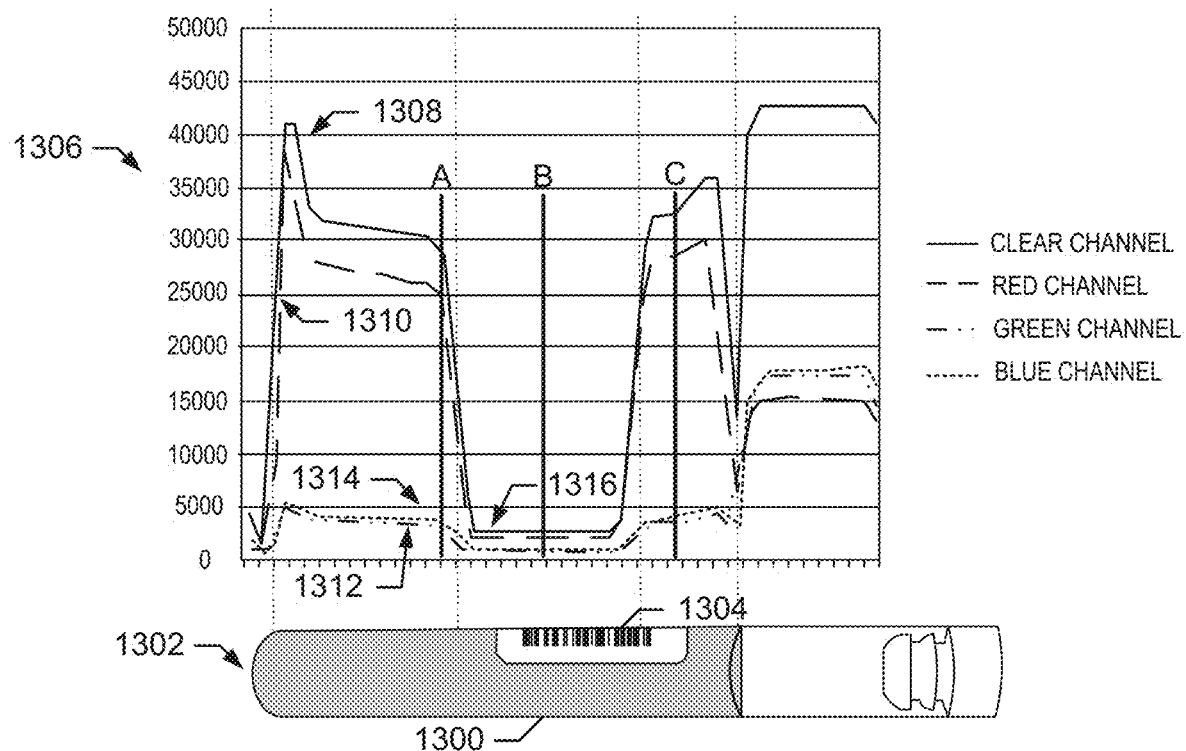
FIG. 13A is a diagram illustrating an analysis of example signal data collected from scanning a calibration sample container using the example system of FIG. 1 for determining the signal restoration coefficient in accordance with the example method of FIG. 12.
Figure 13B:
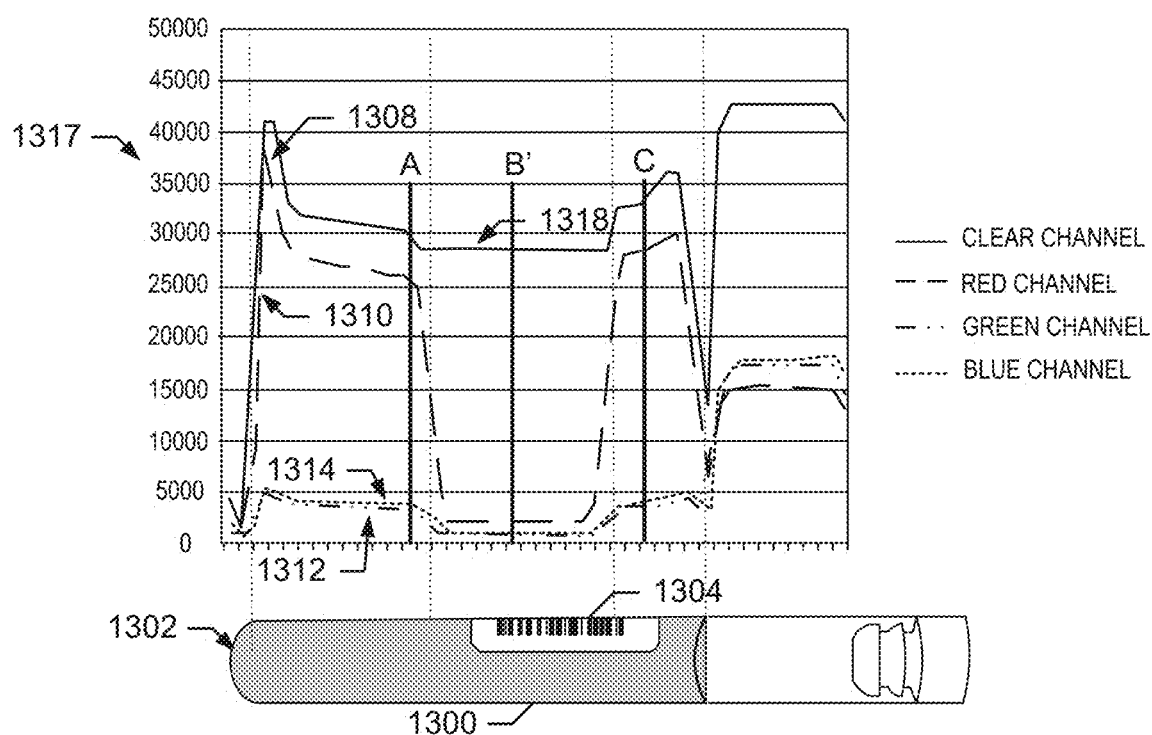
FIG. 13B is a diagram illustrating an example restoration of the signal data of FIG. 13A using the signal restoration coefficient determined using the example method of FIG. 12.

The coefficient table 128 contains a plurality of predetermined signal restoration coefficients for each color signal. The signal restoration coefficients in the coefficient table 128 are determined from calibration data analyzed by the luminance restorer 124. FIG. 12 is an example method for determining one or more signal restoration coefficients for signal data including an attenuated portion due to the presence of one or more labels. FIGS. 13A and 13B are example diagrams illustrating an analysis of signal data collected from scanning a calibration sample 1300 using the example system 100 of FIG. 1. The calibration data of FIGS. 13A and 13B is used to determine the signal restoration coefficient(s) via the example method 1200 of FIG. 12. For illustrative purposes, the example method 1200 of FIG. 12 will be discussed in connection with the example diagrams of FIGS. 13A and 13B. However, the example method 1200 of FIG. 12 can be performed using analyses other than disclosed below in connection with the example diagrams of FIGS. 13A and 13B.

The example method 1200 of FIG. 12 begins with scanning a calibration sample disposed in a sample container having one or more labels affixed to an outer surface of the sample container (block 1202). Referring to FIG. 13A, the calibration sample 1300 is disposed in a sample container 1302 (e.g., the sample container 104 of FIG. 1) having a label 1304 (e.g., the label 202 of FIG. 2) affixed to an outer surface of the sample container 1302. The sample container 1302 containing the calibration sample 1300 is scanned by, for example, the scanner 106 of FIG. 1. The scans include one or more scans and/or scans at different locations along the sample container 1302. Data for each color signal is collected by the sensor(s) 116 and transmitted to the processor 108. For example, graph 1306 includes clear signal data 1308, red signal data 1310, green signal data 1312, and blue signal data 1314. In other examples, the graph includes infrared signal data.

The example method 1200 of FIG. 12 includes detecting a presence of one or more labels on the sample container based on the signal data obtained from the scan (block 1204). In some examples, the presence of the label(s) is identified based on attenuated signal data. Referring again to FIG. 13A, as a result of the label 1304, the color signal data 1308, 1310, 1312, 1314 include attenuated data portions. For example, the clear signal data 1308 includes an attenuated portion 1316, as illustrated in the graph 1306 of FIG. 13A. The label detector 122 detects the presence of the label 1304 based on the determination that the color signal data 1308, 1310, 1312, 1314 includes one or more attenuated data portions (such as the attenuated portion 1316). The attenuated portions can be identified as signal data falling below a threshold for each color signal relative to, for example, signal data collected from portions of the sample container 1302 that do not include the label 1304, or other baseline data such as signal data collected from passing light through air. The label detector 122 detects the number of label(s) 1304 and/or a thickness of the label(s) 1304 based on the color signal data 1308, 1310, 1312, 1314 including respective attenuated portions of the signal data (e.g., the attenuated portion 1316 of the clear signal data 1308) compared to known baseline data.

The example method 1200 of FIG. 12 includes identifying reference points in the scan data for each color signal (block 1206). Using the clear signal data 1308 of FIG. 13A as an example, the luminance restorer 124 identifies a first reference point A in the clear signal data 1308 before the attenuated data portion 1316 begins (i.e., a data point in the data collected before the scanner 106 encounters the label 1304 during scanning of the sample container 1302). The luminance restorer 124 identifies a second reference point B in the clear signal data 1308 substantially at a midpoint of the attenuated data portion 1316 (i.e., a data point falling in the data collected while the scanner 106 scans the label 1304) and a third reference point C in the clear signal data 1308 falling after the attenuated data portion 1316 (i.e., a data point falling in the data collected by the scanner 106 after the label 1304 ends during scanning of the sample container 1302).

The example method 1200 of FIG. 12 includes calculating a signal restoration coefficient for each color signal based on the respective reference points identified for the color signals (block 1208). Using the example clear signal data 1308 of FIG. 13A as an example, the color count values for first reference point A and the third reference point C of the clear signal data 1308 of FIG. 13A are averaged. The resulting value of the average of reference point A and C is divided by the color count value for the second, or center reference point B to determine the signal restoration coefficient. Put another way, the signal restoration coefficient is equal to (A+C)/B.

The example method 1200 of FIG. 12 includes multiplying the attenuated signal data for each color signal, or data corresponding to the locations of the label(s) on the sample container, by a respective signal restoration coefficient for each color signal. For example, referring to the clear signal data 1308 of FIG. 13A, the luminance restorer 124 multiples the color count value of the second reference point B by the signal restoration coefficient to obtain a restored point B' value for the clear signal data 1308, as shown in graph 1317 of FIG. 13B. In some examples, the luminance restorer 124 applies the signal restoration coefficient to one or more other data points in the attenuated data portion 1316 of the clear signal data 1308, such as data points in the attenuated data portion 1316 before the second reference point B and after the second reference point B. Thus, the luminance restorer 124 recreates, interpolates, or restores the portion of the clear signal data 1308 that was attenuated as a result of the presence of the label 1304 on the sample container 1302 based on the surrounding data (e.g., the first reference point A and the third reference point C) corresponding to locations on the sample container 1302 before and after the label 1304. As shown in the graph 1317 of FIG. 13B, after the signal restoration coefficient is applied to the attenuated data portion 1316, the clear signal data 1308 includes a restored data portion 1318.

The luminance restorer 124 determines the signal restoration coefficient for the red, green, and blue color signal data 1310, 1312, 1314 substantially as disclosed above with respect to the clear signal data 1308 (e.g., as disclosed with respect to blocks 1202-1210 of FIG. 12). For example, the luminance restorer 124 identifies reference points in the red signal data 1310 corresponding to locations of the sample container 1302 before the label 1304 (e.g., before an attenuated portion of the red signal data 1310), at the label 1304 (e.g., at substantially a midpoint of the attenuated portion of the red signal data 1310), and after the label 1304 (e.g., after the attenuated portion of the red signal data 1310). The luminance restorer 124 calculates a signal restoration coefficient based on the reference points and applies the signal restoration coefficient to at least a portion of attenuated data in the red signal data 1310 corresponding to location of the label 1304. Thus, the luminance restorer 124 restores the portion of the red signal data 1308 attenuated during scanning.

Referring again to FIG. 12, the example method 1200 includes storing the signal restoration coefficient(s) in a database (block 1212). In some examples, the signal restoration coefficients are stored in a table format by color channel (e.g., clear, red, green, blue). For example, the luminance restorer 124 of FIG. 1 stores the signal restoration coefficients calculated for each color signal 1308, 1310, 1312, 1314 of FIGS. 13A and 13B in the coefficient table 128 of the database 126 of FIG. 1. In some examples, the signal restoration coefficients are stored based on a number of labels 1304 on the sample container 1302 and/or a thickness of the labels. In some examples, the coefficient table 128 includes two or more tables including a first table storing the reference points in the attenuated data used to calculate the signal restoration coefficients for each color or, more generally, color counts before and after the attenuated portions for each color signal, and a second table including the signal restoration coefficients calculated based on the respective reference points. The luminance restorer 124 can also store other information in the coefficient table 128 and/or the database 126, such as the position of the label(s) 1304 on the sample container 1302 as determined based an analysis of signal data indicative of the label relative to signal data indicative of a bottom of the sample container 1302.

The example method 1200 includes determining whether another calibration sample is to be analyzed to determine signal restoration coefficients (block 1214). If another calibration sample is to be analyzed, the example method 1200 scans the other calibration sample and calculates the signal restoration coefficients as disclosed above in connection with blocks 1202-1210. For example, the luminance restorer 124 determines signal restoration coefficients for a calibration sample disposed in a sample container having more than one label 1304 affixed to the outer surface thereof and/or having a label with a different thickness than the example label 1304 of the sample container 1302 of FIGS. 13A and 13B. The luminance restorer 124 calculates signal restoration coefficients for calibration samples, including calibration samples having different coloration. The luminance restorer 124 stores the signal restoration coefficients determined from the calibration samples in the coefficient table 128 (e.g., as disclosed above with respect to block 1214 of the example method 1200 of FIG. 12). Thus, the luminance restorer 124 builds a table (e.g. the coefficient table 128) of signal restoration coefficients determined from calibration samples.

During scanning of non-calibration samples such as the sample 102 disposed in the sample container 104 of FIG. 2-11, the luminance restorer 124 queries the coefficient table 128 based the presence of attenuated portions in the signal data indicative of one or more label(s) 202 on the sample container 104 to identify a signal restoration coefficient. Using the clear signal data 1108 of FIG. 11 as an example, the luminance restorer 124 identifies data points in the clear signal data 1108 before and after the attenuated portion 1110. The luminance restorer also identifies the number of label(s) 202 on the sample container 104 and/or the thickness of the label(s) 202. The luminance restorer 124 looks up a signal restoration coefficient for the attenuated portion 1110 from the coefficient table 128 based on the data points in the clear signal data 1108 and the number of label(s) 202 and/or the thickness of the label(s) 202. For example, the luminance restorer 124 queries the coefficient table 128 for reference points that are within a threshold range of data points identified in the clear signal data 1108 and that were obtained from signal data collected from a sample container having a same number of labels as the label(s) 202 detected on the sample container 104. The luminance restorer 124 identifies the signal restoration coefficient corresponding to the reference points and number of labels 202 from the coefficient table 128. The luminance restorer 124 applies the selected signal restoration coefficient to the attenuated portion 1110 of the clear signal data 1108. For example, the luminance restorer 124 multiples color count values in the attenuated portion 1110 by the selected signal restoration coefficient to generate color count values that can be interpolated into the clear signal data 1108 to replace the attenuated portion 1110.

Figure 14:
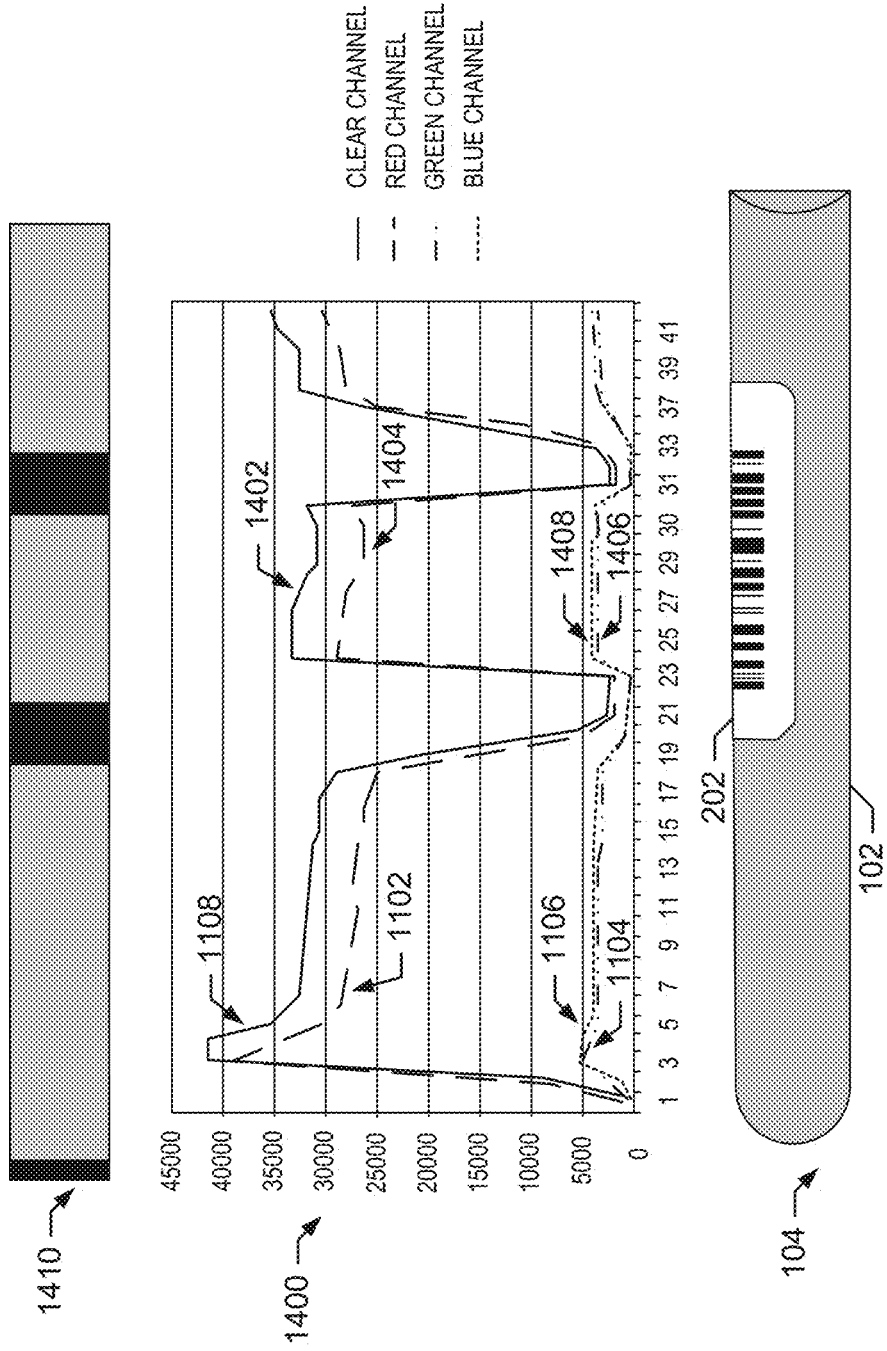
FIG. 14 is a diagram illustrating an example restoration of the signal data of FIG. 11 using the signal restoration coefficient determined using the example method of FIG. 12.

FIG. 14 is a diagram showing the restoration of the attenuated portions 1110 of the red, green, blue, and clear signal data 1102, 1104, 1106, 1108 of FIG. 11. As shown in graph 1400 of FIG. 14, the clear signal data 1108 includes a clear signal restored or interpolated portion 1402 calculated from the application of the selected signal restoration coefficient for the clear signal data 1108 to the attenuated portion 1110 of FIG. 11. Thus, the clear signal data 1108 is restored such that the clear signal data 1108 is substantially equivalent to clear signal data that would be collected from the scanning of the sample container 104 and the sample 102 if there was no label(s) 202 on the sample container 104. As also shown in the example graph 1400 of FIG. 14, the luminance restorer 124 restores attenuated data portions of the red signal data 1102 to create a red signal restored portion 1404, the green signal data 1104 to create a green signal restored portion 1406, and the blue signal data 1106 to create a blue signal restored portion 1408 substantially as disclosed above with respect to the restoration of the attenuated portion 1110 of the clear signal data 1108.

The data analyzer 120 generates a digital sample representation 1410 based on the signal data 1102, 1104, 1106, 1108, including the restored portions 1402, 1404, 1406, 1408 of the red, green, blue, and clear signal data 1102, 1104, 1106, 1108. As a result of the application of the signal restoration coefficient to the attenuated portions 1110 of the red, green, blue, and clear signal data 1102, 1104, 1106, 1108, the sample representation 1410 contains less interrupted or shadowed portions as compared to the sample representation 1112 of FIG. 11 generated before application of the signal restoration coefficient (e.g., the interrupted portion 1114). Rather, the shadowed portion is substantially restored and can be represented, for example, by the algorithm $RGB_{Value} * Luminance_{Percentage} * xLabel_{Coefficient}$, where "$xLabel_{Coefficient}$" is the signal restoration coefficient for the number of labels 202 detected on the sample container 104. The sample representation 1410 contains a more complete representation of the sample 102 and/or the sample container 104 as compared to the sample representation 1112 of FIG. 11.

Thus, the luminance restorer 124 automatically retrieves a signal restoration coefficient from the coefficient table 128 upon detection of one or more label(s) 202 on the sample container 104 and applies the signal restoration coefficient to attenuated data portions in signal data collected during the scanning of the sample container 104 to restore the attenuated data. The data analyzer 120 generates a sample representation using the restored signal data that is substantially equivalent to a sample representation that would be generated for the sample container 104 if the sample container 104 did not include one or more label(s) 202. In examples where the label 202 covers a substantial portion of the sample container 104 (e.g., an entire length of the sample container 104), the luminance restorer 124 can apply the respective signal restoration coefficient to respective portions of the attenuated signal data 1102, 1104, 1106, 1108 based on, for example, a volume of the sample 102 in the sample container 104 to restore at least a portion of an area of interest of the sample container 104.

In some examples, the processor 108 analyzes the sample representation 1410 of FIG. 14 to determine a sample integrity of the sample 102 for further processing. Also, in some examples, the sampler transporter 110 of the scanner 106 moves the sample container 104 in the scanner 106 to collect additional data with respect to the sample container 104 and/or the sample 102. For example, to determine a color of the stopper 208 of the sample container 104, the sample transporter 110 positions the sample container 104 in the scanner 106 for scanning of the stopper 208 of the sample container 104 by the light source(s) 112. Thus, in addition to scanning a length of the sample container 104 to detect a presence of one or more labels 202 on the sample container 104 as part of the luminance restoration, the example system 100 can be used to analyze specific areas of interest with respect to the sample 102 and/or the sample container 104. In other examples, the processor 108 determines the sample integrity of the sample 102 using data that is not restored, such as data collected from scanning the sample container 104 above or below one or more of the labels 202.

For example, a color of at least a portion of the sample 102 as represented in the sample representation 1410 can be determined based on values corresponding to the red, green, and blue signal data collected during one or more scans. The HIL analyzer 130 detects any variations in intensity (e.g., saturation) of the color and assigns a level (e.g., a numerical level) representative of, for example, a level of hemolysis (or icterus or lipemia) of the sample 102. In some examples, the HIL analyzer 130 calculates the hemolysis level for the sample based on the sample color and/or intensity as compared to previously collected color and/or absorbance data stored in a table of the HIL analyzer 130. In some such examples, the HIL analyzer 130 assigns numerical ranking(s) representative of a degree of hemolysis to the sample 102 (e.g., a ranking from 1-4). If HIL analyzer 130 determines that the hemolysis level is greater than a predetermined threshold, the HIL analyzer 130 identifies the sample 102 as an exception.

The sample layer analyzer 132 of the processor 108 also uses color data collected from scanning the sample 102 to analyze centrifugation efficacy of the sample 102. The sample layer analyzer 132 can identify layers in the sample based on, for example, changes in the color of the sample detected during the scan. If the sample 102 is not substantially completely centrifuged in the sample container 104, one or more layers of the sample 102 will include white and/or red blood cells that can be detected based on an analysis of signal absorption and/or color of the sample 102 as represented, for example, in the sample representation 1410. For example, a change in color or an unexpected color detected in a layer in the sample 102 can indicate that the sample 102 is not completely centrifuged. In other examples, the sample layer analyzer 132 analyzes the scan data to determine if a border between a first layer in the sample and a second layer in the sample 102 is sharp. For example, the sharpness of the border can be determined by a comparison of a color gradient between the first and second layers. If the sample layer analyzer 132 detects that one or more layers of the sample 102 contain white and/or red blood cells or that the layers are not well-defined, the sample layer analyzer 132 identifies the sample 102 as an exception.

In addition to analyzing the sample 102 with respect to HIL and centrifugation efficacy based on color and/or signal absorption data, the processor 108 also analyzes the sample 102 and/or the sample container 104 with respect to properties such as sample volume and cap color. The sample volume analyzer 134 of the processor 108 determines an amount of the sample 102 in the sample container 104 above a gel separator to determine if there is sufficient volume of the sample 102 based on, for example, scan data indicating a presence of the sample 102 in the sample container 104 versus air. If the sample volume analyzer 134 determines that there is not sufficient volume of the sample 102, the sample volume analyzer 134 identifies the sample 102 as an exception.

As another example, the container analyzer 136 analyzes signal data collected from scanning the container stopper 208 to determine if the sample container 104 has a properly colored container stopper 208. For example, the container analyzer 136 can retrieve information input by a user via the graphical user interface 140 associated with the processor 108 and stored in the database 126 with respect to the intended testing for the sample 102. The container analyzer 136 compares the detected color of the container stopper 208 (e.g., as disclosed above with respect to the example scanner 800 of FIG. 8 for detecting cap color based on reflection of light) to an expected color of the stopper 208 based on the intended testing. If the color of the container stopper 208 does not match the expected color, the container analyzer 136 identifies the sample container 104 as an exception.

Based on the analysis performed by the HIL analyzer 130, the sample layer analyzer 132, the sample volume analyzer 134, and the container analyzer 136, the quality evaluator 138 determines a quality indicator for the sample 102. The quality indicator identifies the sample 102 as acceptable for routine or intended testing or as an exception. For example, if any of the HIL analyzer 130, the sample layer analyzer 132, the sample volume analyzer 134, and/or the container analyzer 136 identifies the sample 102 and/or the sample container 104 as an exception, then the quality evaluator 138 may output a quality indicator that identifies the sample 102 as requiring exception handling. The quality indicator generated by the quality evaluator 138 is viewable by a user via the graphical user interface 140 associated with the processor 108.

In some examples, the quality indicator output by the quality evaluator 138 is a symbol such as a checkbox or an "X" mark indicating whether the sample 102 is acceptable for further testing as planned or if the sample 102 is an exception. In some examples, the quality evaluator 138 outputs a numerical ranking of the quality of the sample 102. For example, the quality evaluator 138 can assign the sample 102 a value of "1" if there are no issues identified by the HIL analyzer 130, the sample layer analyzer 132, the sample volume analyzer 134, and/or the container analyzer 136, the quality evaluator 138. The quality evaluator 138 can assign the sample a value of "2" if at least one of the analyzers 130, 132, 134, 136 identified an issue with the sample 102 and a value of "3" if more than one issue was identified by the analyzers 130, 132, 134, 136. In some examples, the criteria used to assign the numerical rankings to the sample 102 are input by a user via the graphical user interface 140. Based on the output by the quality evaluator 138 and viewed by a user via the graphical user interface 140, the user can determine how the sample 102 should be handled for further testing.

Figure 15:
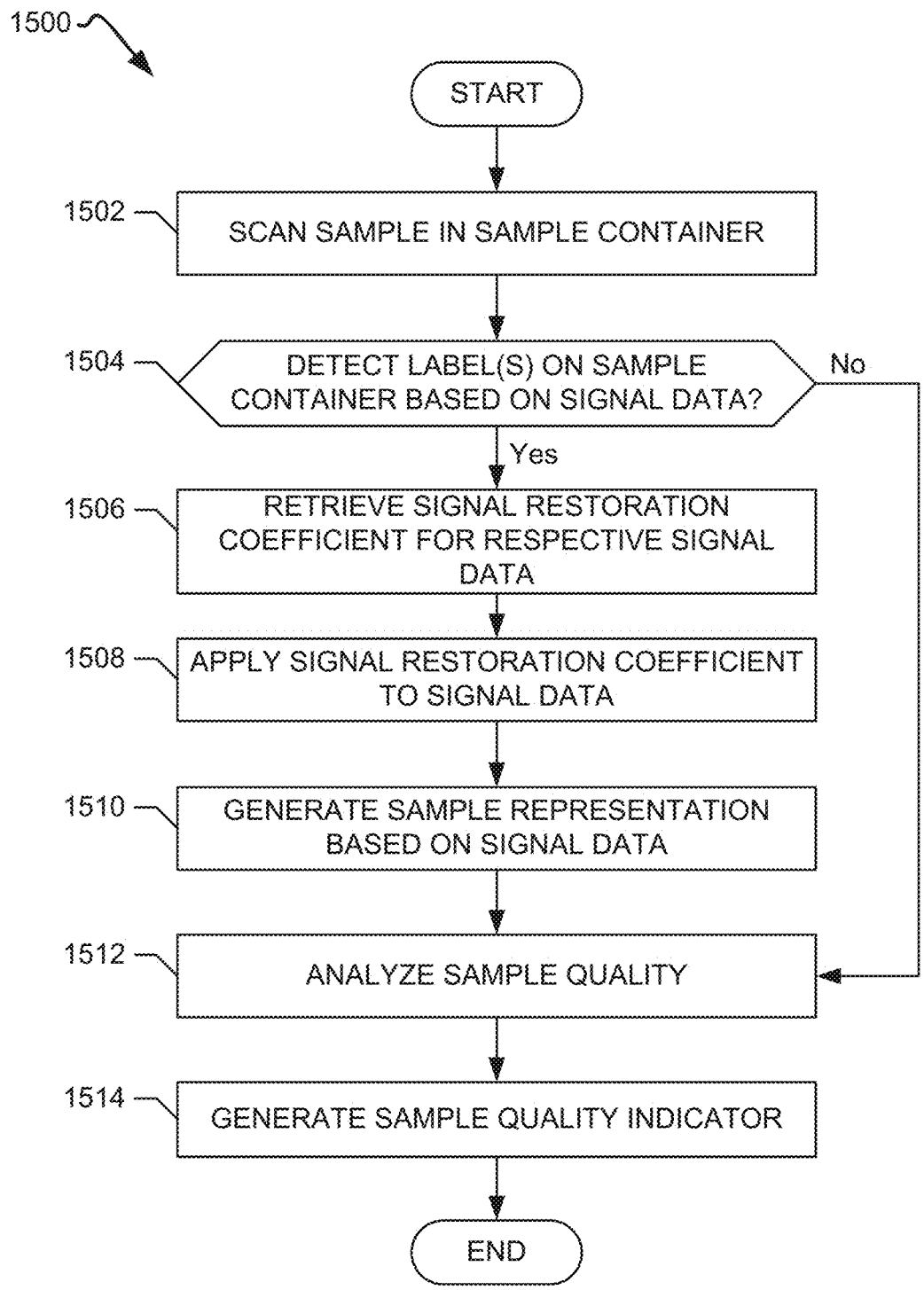
FIG. 15 is a flow diagram of an example method for evaluating sample integrity that can be used to implement the examples disclosed herein.

FIG. 15 depicts an example flow diagram representative of an example method 1500 for analyzing an integrity of a sample. The example method 1500 includes scanning a sample disposed in a sample container (block 1502). For example, the scanner 106, 300, 600, 700, 800 of FIGS. 1-8 scans the sample 102, 1300 disposed in the sample container 104, 1302 of FIG. 1-11, 13, 14 using one or more light source(s) 112. In some examples, the scanner 106, 300, 600, 700, 800 scans a length of the sample container 104, 1302. The scan can include one or more scans at one more locations along the sample container 104, 1302.

In the example method 1500, scanning the sample disposed in the sample container generates signal data corresponding to different color channels of the light source(s) 112, such as red, green, blue, and clear color signals. The scan data is processed and/or analyzed by, for example, the data analyzer 120 of the processor 108 of FIG. 1. The example method 1500 includes detecting whether the sample container includes one or more label(s) (block 1504). In the example method 1500, if the signal data includes color signal data that is attenuated or falls below a predetermined threshold along a length of the sample container 104, the example method 1500 determines that the sample container 104 includes one or more labels. For example, if the label detector 122 of the example system 100 of FIG. 1 detects attenuated portions such as the attenuated portion 1110, 1316 of the signal data 1102, 1104, 1106, 1108, 1308, 1310, 1312, 1314 of FIGS. 11, 13A, and 13B, the label detector 122 determines that the sample container 104, 1302 includes a label 202, 1304. In some examples, the label detector 122 determines a number of the label(s) 202 and/or a thickness of the label(s) 202 by comparing the attenuated signal data portions to baseline data corresponding to non-label locations of the sample container 104. In other examples, the label detector 122 determines that the sample container 104 includes the label 202, 1304 if substantially all or nearly all of the signal data is attenuated signal data. In such examples, the label 202 may extend along a substantial portion of the sample container 104 (e.g., substantially along the entire length of the sample container 104).

If a label is detected on the sample container, the example method 1500 continues with retrieving a signal restoration coefficient for restoring the respective color signal data (block 1506). The example method 1500 can include retrieving the signal restoration coefficient from a database including signal restoration coefficients for calibration sample data generated substantially as disclosed above in connection with the example method 1200 of FIG. 12. For example, the luminance restorer 124 of FIG. 1 looks up signal restoration coefficients for each color channel (e.g., clear, red, green, blue) from the coefficient table 128 of the database 126 based on one more variables, including, for example, the number of label(s) 202 and/or the thickness of the label(s) 202 and data points in the respective signal data, such as data points (e.g., color counts) in the attenuated portions of the respective signal data. The luminance restorer 124 identifies the signal restoration coefficient corresponding to the number of label(s) 202, the thickness of the label(s) 202, and/or the data points relative to calibration data used to generate the signal restoration coefficients in the coefficient table 128.

The example method 1500 includes applying the selected signal restoration coefficient to the respective color signal data, such as to attenuated portions of the signal data (block 1508). For example, the luminance restorer 124 multiples the values of the attenuated portions 1110 of the red, green, blue, and clear signal data 1102, 1104, 1106, 1108 of FIG. 11 by the respective signal restoration coefficients to generate the restored portions 1402, 1404, 1406, 1408 as illustrated in FIG. 14. In some examples, the signal restoration coefficients are applied to only portions of the attenuated portions 1110 of the red, green, blue, and clear signal data 1102, 1104, 1106, 1108 based on, for example, the volume of the sample 102 in the sample container 104 to restore at least a portion of an area of interest of the sample container 104.

The example method 1500 includes generating a sample representation based on the signal data, including the restored portions (block 1510). For example, the data analyzer 120 of FIG. 1 generates a digital sample representation 1410 based on the signal data 1102, 1104, 1106, 1108, including the restored portions 1402, 1404, 1406, 1408 of the red, green, blue and clear signal data 1102, 1104, 1106, 1108. In generating the sample representation 1410, the data analyzer 120 accounts for a luminance percentage value in addition to the signal data restored based on the signal restoration coefficient to account for a brightness of the light passing through the sample 102.

Thus, the example method 1500 accounts for the presence of the label(s) 202 by restoring the signal data attenuated due to the presence of the label(s) 202 in the path of the light during scanning of the sample 102. The restoration of the attenuated signal data provides for analysis of the sample 102 that is substantially equivalent to an analysis of the sample 102 if there were not any label(s) 202 on the sample container 104.

After restoration of the signal data or, if no label detected on the sample container (e.g., at block 1504), the example method 1500 continues with analyzing the sample with respect to sample quality (block 1512). Analyzing the quality of the sample can include performing a HIL analysis, determining whether there is sufficient sample volume for testing, and/or checking a color of a cap of the sample container. For example, using the restored color signal data, the HIL analyzer 130 of the processor 108 of FIG. 1 analyzes hemolysis levels of the sample 102 to determine whether testing of the sample 102 should proceed or whether the sample 102 should be treated as an exception. The sample layer analyzer 132 of the processor 108 of FIG. 1 analyzes the color signal data to detect the presence of white and/or red blood cells in the sample 102, which can indicate incomplete separation of layers of the sample 102 during centrifugation. As another example, the sample volume analyzer 134 can determine whether there is a sufficient volume of the sample 102 based on an analysis of signal data indicating a presence of the sample 102 as compared to air in the sample container 104. Also, the example scanner 106 can position the sample container 104 to scan the stopper 208 of the sample container 104 to enable verification of a color of the stopper 208 by the container analyzer 136.

The example method 1500 includes generating a sample quality indicator based on the analysis of the sample quality (block 1514). In some examples, the sample quality indicator is a symbol (e.g. a checkmark or an "X" mark) or a numerical value that indicates whether the sample can be treated as a routine sample or is an exception. The sample quality indicator can be output for viewing by a user via a graphical user interface. For example, if the analysis of the sample identifies an issue with the sample, such as insufficient volume or hemolysis levels that are higher than a predetermined threshold, then the example method 1500 includes generating a sample quality indicator that identifies the sample as an exception. If the analysis of the sample does not identify any issues with the sample, the example method 1500 includes generating a sample quality indicator that indicates the sample is adequate for further testing. The sample quality indicator can be generated by, for example, the quality evaluator 138 of the processor 108 of FIG. 1 and viewed via, for example, the graphical user interface 140 associated with the processor 108 of FIG. 1.

Thus, the example method 1500 provides for scanning of a sample to analyze the adequacy or integrity of the sample and/or the sample container for testing of the sample. The example method 1500 automatically detects the presence of a label on the sample container and dynamically retrieves a signal restoration coefficient to restore the signal data affected by the label. Rather than requiring the sample container to be positioned by a user or an analyzer in the scanner in a certain position to avoid interference from the label during scanning, the example method 1500 automatically accounts for the label during processing of the signal data. Thus, the example method 1500 provides for efficient analysis of the sample disposed in a sample container with or without a label.

As disclosed above, the sample container 104 is scanned by the scanner 106 to determine a quality of the sample 102 and/or the sample container 104 for processing in, for example, a clinical analyzer. The scanner 106 can be implemented with a clinical analyzer system to efficiently evaluate samples before the sample container 104 reaches the clinical analyzer. As disclosed above with respect to FIG. 2, in some examples, the sample container 104 is placed in the sample transporter 110 of the scanner 106 by, for example, a user or a robotic machine, prior to the sample container 104 being processed by a clinical analyzer. For example, the sample container 104 can be removed from a sample carrier track coupled to the clinical analyzer by a robotic arm, placed in the sample transporter 110 of the scanner 106 for scanning, and then returned to the track by the robotic arm for delivery to the analyzer for processing based on the sample quality indicator for the sample 102 and/or the sample container 104. In other examples, the scanner 106 is coupled to (e.g., integrated with) the sample carrier track. In such examples, the scanner 106 scans the sample container 104 as the sample container 104 moves along the track.

Figure 16:
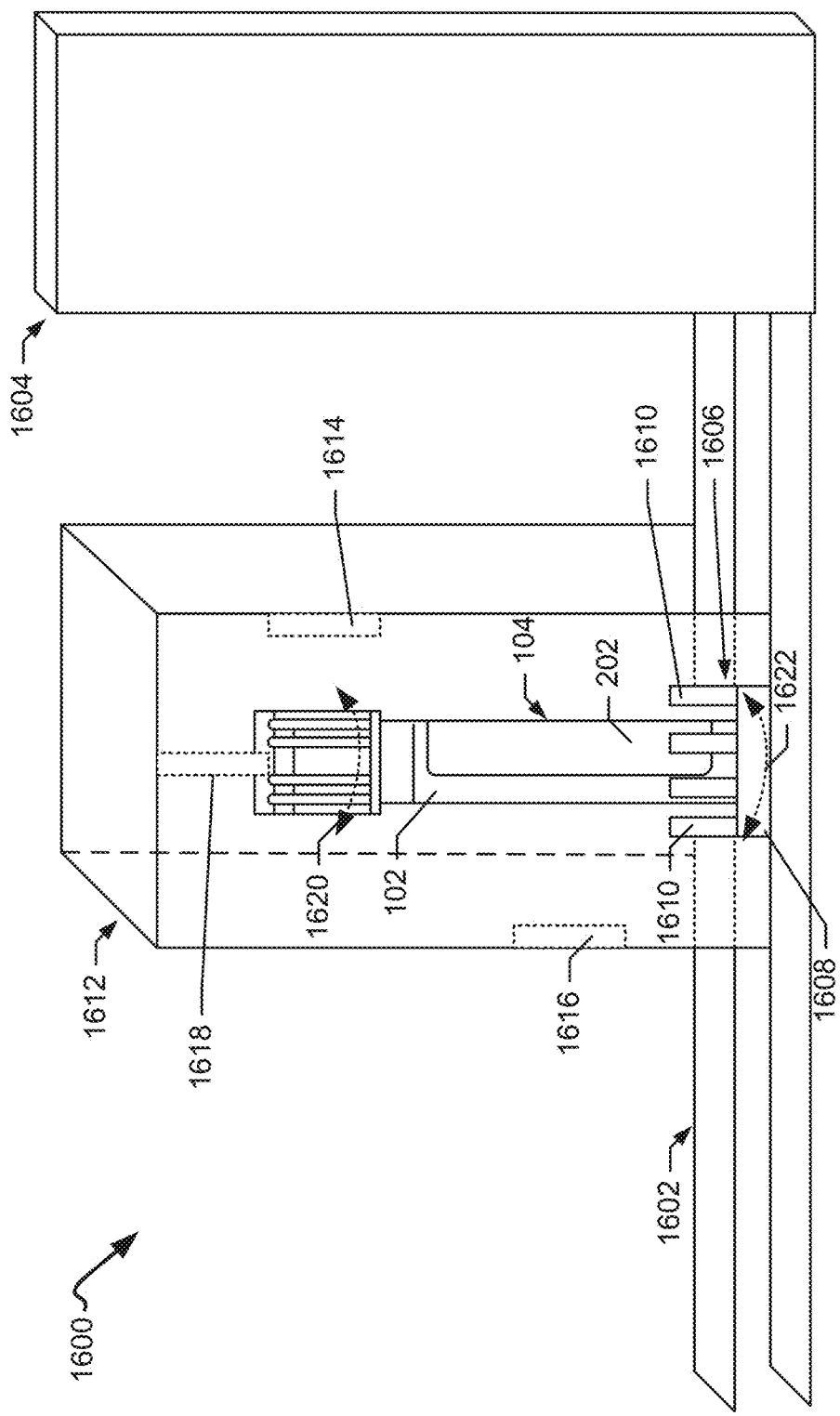
FIG. 16 is a schematic, partial side view illustration of an example sample tube carrier track including a scanner that can be used to implement the examples disclosed herein.

FIG. 16 illustrates an example system 1600 in which the sample container 104 is disposed on a sample carrier track 1602 for delivery to an analyzer 1604 for processing. The sample container 104 includes the sample 102 and at least one label 202 affixed to a surface of the sample container 104. One or more other sample containers can also be disposed on the track 1602 at the same time the sample container 104 is disposed on the track 1602. As illustrated in FIG. 16, the sample container 104 is disposed in a carrier 1606 coupled to the track 1602. The sample container 104 is placed in the carrier 1606 (e.g., by a robotic arm) and the carrier 1606 holds the sample container 104 as the sample container 104 moves along the track 1602.

The example carrier 1606 of FIG. 16 includes a base 1608 and fingers 1610 for holding the sample container 104. The fingers 1610 secure the sample container 104 in the carrier 1606 (e.g., in an upright, vertical position). For example, the fingers can be spring-loaded to secure the sample container 104 and/or other containers having varying diameters or shapes. The base 1608 and/or the fingers 1610 can be plastic and/or metal. Although four fingers 1610 are shown in FIG. 16, the carrier 1606 can include additional or fewer fingers 1610.

In the example system 1600, as the carrier 1606 moves along the track 1602 with the sample container 104 disposed therein, the carrier 1606 passes through a scanner 1612. The scanner 1612 includes one or more light source(s) 1614 (e.g., the light source(s) 112 of the example scanner 106 of FIG. 1) and one or more sensor(s) 1616 (e.g., the sensor(s) 116 of the example scanner 106 of FIG. 1). The scanner 1612 can include one or more other components, such as optics, as disclosed above in connection with the example scanners 106, 300, 500, 600, 700, 800 of FIGS. 1-8.

When the carrier 1606 enters the scanner 1612, the track 1602 can stop or pause movement for a period of time to allow the scanner 1612 to scan the sample container 104 disposed in the carrier 1606. The scanner 1612 scans the sample container 104 as disclosed above in connection with FIGS. 1-15. For example, the light source(s) 1614 emit light that passes through the sample container 104 and is collected by the sensor(s) 1616 as signal data. As disclosed above, in some examples, at least a portion of the light emitted by the light source(s) 1614 passes through the label 202 on the sample container 104. The signal data collected by the sensor(s) 1616 is processed by a processor (e.g., the processor 108 of FIG. 1) to determine a quality of the sample 102 and/or the sample container 104 as disclosed above in connection with FIGS. 1-15. In some examples, the signal data collected by the scanner 1612 includes one or more attenuated portions due to the presence of the label 202. The processor restores the attenuated signal portions using a signal restoration coefficient, as disclosed above in connection with FIGS. 10-15.

In some examples, prior to the scanner 1612 scanning the sample container 104, the position of the sample container 104 in the carrier 1606 and/or the position of the carrier 1606 is adjusted to avoid interference from the fingers 1610 of the carrier 1606 during scanning. In some examples, if the light source(s) 1614 of the scanner 1612 emit light that passes through one or more of the fingers 1610 of the carrier 1606, the signal data collected by the sensor(s) 1616 of the scanner 1612 includes attenuated signal data because the light does not pass through the finger(s) 1610 of the carrier 1606. Thus, to maximize an area of the sample container that is scanned by the scanner 1612, the scanner 1612 adjusts the position of the sample container 104 such that the light emitted by the light source(s) 1614 passes substantially through the sample container 104 and not the finger(s) 1610.

For example, the scanner 1612 can include a positioner 1618 to adjust a position of the sample container 104 in the carrier 1606. In some examples, the positioner 1618 rotates the sample container 104 in the carrier 1606 to align the sample container 104 relative to the light source(s) 1614 (as represented by the arrow 1620 of FIG. 16). As a result of the positioning of the sample container 104 by the positioner 1618, the light emitted by the light source(s) 1614 passes between two of the fingers 1610 rather than through the fingers 1610. In other examples, the positioner 1618 holds the sample container 104 stationary while the base 1608 of the carrier 1606 rotates (e.g., via the track 1602, as represented by the arrow 1622 of FIG. 16). Thus, as a result of the positioning of the sample container 104 and/or the carrier 1606, the light passes substantially through the sample container 104 (including, in some examples, the label 202) rather than the fingers 1610. Therefore, the signal data collected from scanning the sample container 104 that is used to determine a quality of the sample 102 and/or the sample container 104 is greater in amount and/or of increased quality as compared to signal data collected if the light passes through the finger(s) 1610 and the sample container 104.

After the scanner 1612 has scanned the sample container 104, the carrier 1606 moves the sample container 104 out of the scanner 1612 via the track 1602. In some examples, the sample container 104 is removed from the track 1602 (e.g., via a robotic arm) based on the sample quality analysis of the signal data, including any restored signal portions due to the label 202. For example, if the sample quality indicator generated by the processor indicates an issue with a volume of the sample 102 or a hemolysis level of the sample 102, the sample container 104 may be removed from the track 1602 before reaching the analyzer 1604. In other examples, the sample container 104 proceeds via the track 1602 for further processing by the analyzer 1604 if no sample quality issues are detected based on the analysis of the signal data.

Thus, as illustrated in FIG. 16, the scanner 106 of the example system 100 can be integrated with a track of a clinical analyzer system for efficient analysis of the sample container before processing by the analyzer. In such examples, a position of the sample container can be adjusted so as to avoid interference from, for example, a sample container carrier, to maximize an amount signal data and/or the quality of the signal data collected from the sample container during scanning. In other examples, the scanner 106 of the example system 100 is separate from the track, such that sample containers are moved to and from the track for scanning. In examples where the sample container is scanned while on the track or in examples where the sample container is removed from the track for scanning, the disclosed examples account for any labels on the sample container by restoring the signal data affected by the presence of the label during data processing, thereby providing robust data for sample quality analysis.

Example scanners disclosed herein include light emitter(s) (e.g., the light emitter(s) 306, 608 of FIGS. 3-6) and sensor(s) (e.g., the sensors 316, 618 of FIGS. 3-6) disposed relative to a sample container such that the sensor(s) detect light emitted by the light emitter(s) and passing through the sample container. In some examples disclosed herein, the light emitter(s) and the sensor(s) are disposed substantially opposite from one other relative to the sample container. Put another way, the emitter(s) may be located on a first side of the sample container and the sensor(s) may be located on a second side of the sample container opposite the first side (e.g., as illustrated in FIGS. 3, 6). In other examples, a scanner includes a plurality of arrays including light emitter(s) and sensor(s) coupled to each array. In such examples, the arrays are distributed relative to the sample container.

Figure 17:
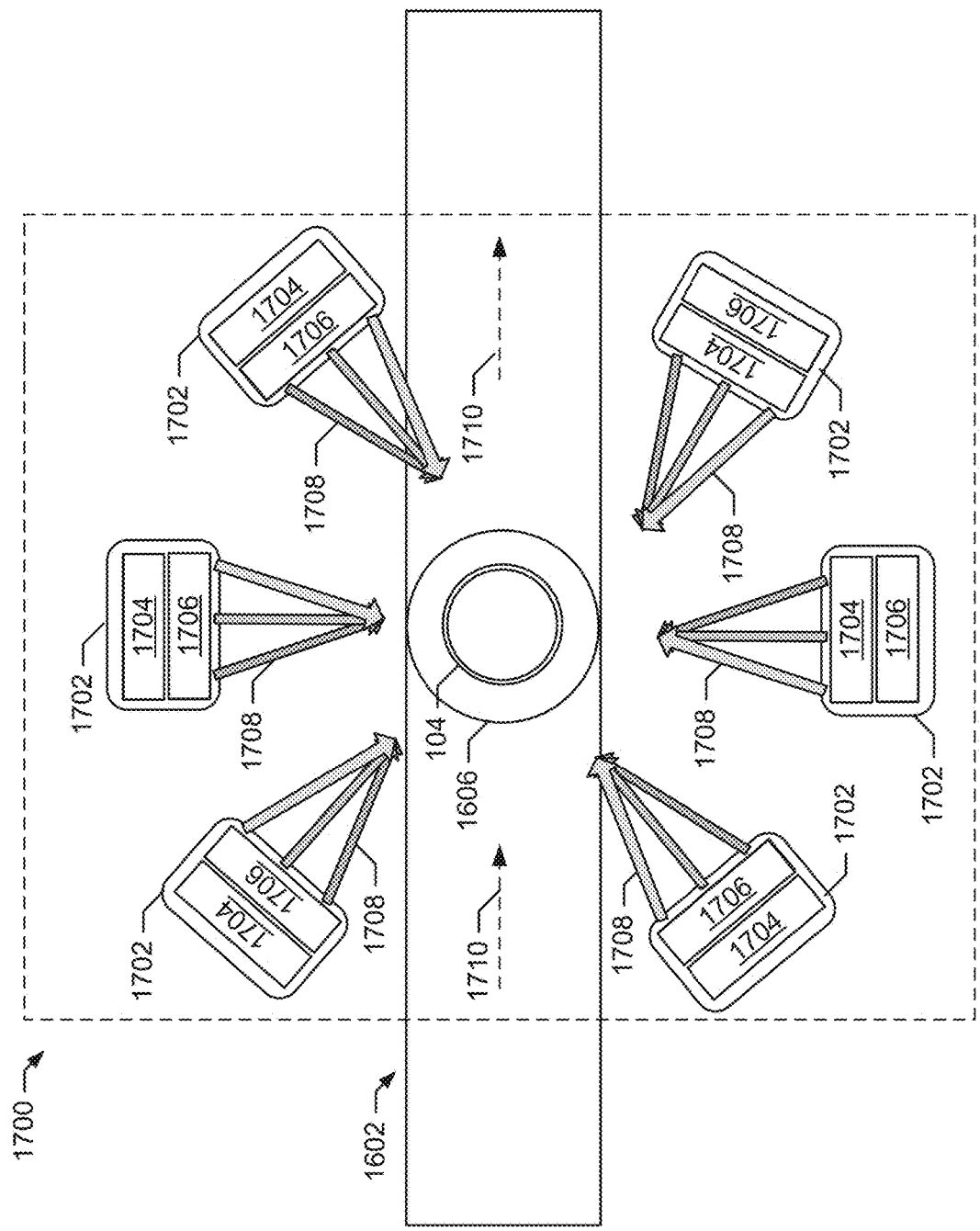
FIG. 17 is a schematic, top view illustration of an example scanner that may be implemented with the example track of FIG. 16.

FIG. 17 is a schematic, top view illustration of an example scanner 1700 including a plurality of emitter/sensor arrays 1702 disposed about the sample container 104 in the example carrier 1606 of FIG. 16. As illustrated in FIG. 17, the carrier 1606 is coupled to the sample carrier track 1602 of FIG. 16.

The example scanner 1700 of FIG. 17 includes a plurality of emitter/sensor arrays 1702. Each emitter/sensor array 1702 includes one or more light emitters 1704 and one or more sensors 1706 (e.g., digital color sensor(s)). In the example of FIG. 17, the emitter/sensor arrays 1704 are distributed in a substantially circular shape about the sample container 104. The example scanner 1700 of FIG. 17 can include different numbers of emitter/sensor arrays 1702 and/or different arrangements of the arrays 1702. In some examples, one or more of the emitter/sensor arrays 1702 are disposed in a different plane relative to the sample container 104 than another one of the emitter/sensor arrays 1702. In other examples, all of the emitter/sensor arrays 1702 are disposed in substantially the same plane.

The light emitter(s) 1704 of the example array(s) 1702 emit one or more beams 1708 of light. The light beam(s) 1708 can include light having different wavelengths (e.g., wavelengths corresponding to red light, green light, or blue light), as disclosed above. The light beam(s) 1708 are transmitted to the sample container 104 such that a path of the light beam(s) 1708 intersects the sample container 104. The sensor(s) 1706 of one or more emitter/sensor arrays 1702 detects the light passing through the sample container 104, scattered by a sample in the sample container 104 (e.g., the sample 102), reflected by the sample, etc. In some examples, the emitter/sensor array 1702 including the sensor(s) 1706 that detect the light passing through the sample container 104 is disposed substantially opposite the emitter/sensor array 1702 including the light emitter(s) 1704 that emitted the light detected by the sensor(s) 1706. In some examples, the emitter/sensor array(s) 1702 including the sensor(s) 1706 that detect the light passing through the sample container 104 include light emitter(s) 1704 that emit light beam(s) 1708 at substantially the same time as the sensor(s) 1706 detect the light beam(s) 1708 passing through the sample container 104. In other examples, the light emitter(s) 1708 of an emitter/sensor array 1702 emit light at a different time than the sensor(s) 1706 of the emitter/sensor array 1702 detect light passing through the sample container 104.

In the example of FIG. 17, the substantially circular distribution of the emitter/sensor arrays 1704 about the sample container 104 provides for data to be collected from different angles relative to a portion of the sample container 104. For example, when the emitter/sensor arrays 1702 are disposed about the sample container 104 within substantially the same plane, the light beam(s) 1708 emitted by the light emitter(s) 1704 pass through substantially the same portion of the sample container 104 at different angles, are reflected by or scattered by the substantially the same portion of the sample in the sample container 104 at different angles, etc. The signal data generated by the sensor(s) 1706 distributed about the sample container 104 can be used to generate a composite image of the portion of the sample container 104 exposed to the light beam(s) 1708 (e.g., via a processor such as the processor 108 of FIG. 1).

The integrity of the sample disposed in the sample container 104 and/or characteristics of the sample container 104 (e.g., cap color) can be determined based on the composite image generated for the portion of the sample container 104 based on the signal data collected different angles relative to the sample container 104. The signal data collected by the sensor(s) 1706 is processed by a processor (e.g., the processor 108 of FIG. 1) to determine a quality of the sample and/or the sample container 104 as disclosed above in connection with FIGS. 1-15. For example, the composite image generated for the portion of the sample container 104 based on the signal data collected different angles relative to the sample container 104 can be used to detect the presence of microclots in the sample due to, for example, improper mixing of the sample container 104. As another example, the processor can detect clotting (e.g., microclots) in the sample based on the detection of, for example, light scattering by the sensor(s) 1702. In some examples, the signal data collected by the scanner 1612 includes one or more attenuated portions due to the presence of a label (e.g., the label 202) on the sample container 104 and the position of the emitter/sensor arrays 1702 relative to the label. The processor restores the attenuated signal portions using a signal restoration coefficient, as disclosed above in connection with FIGS. 10-15. In some examples, the emitter/sensor arrays 1702 are disposed in different planes to collect data for two or more portions of the sample container 104 and composite images can be generated for the respective portions.

Thus, in some examples, the sample and/or the sample container 104 can be evaluated without scanning the sample container 104 along a longitudinal axis of the sample container 104. Instead, the sample and/or the sample container 104 can be analyzed based on a composite image generated from signal data collected from different angles of a portion of the sample container. Such examples including emitter/sensor arrays 1702 distributed about a sample container 104 may be used in examples when the sample container 104 is disposed on or moving via the track 1602, as represented by the arrows 1710 of FIG. 17. In such examples, providing a scanner that scans the sample container 104 along the longitudinal axis of the sample container 104 may not be feasible and/or may be disruptive to efficient movement of a plurality of sample containers via the track 1602. In such examples, collecting data for a portion of the sample container 104 from several different angles can provide an indication of integrity of the sample and/or the sample container.

Although the example scanner 1700 of FIG. 17 is discussed in connection with the example carrier 1606 and track 1602 of FIG. 16, the example scanner 1700 can be implemented in an analyzer or other laboratory apparatus. Also, the example emitter/sensor arrays 1702 of FIG. 17 can be implemented with any of the example scanners of FIGS. 1-8 and 16. For example, the emitter/sensor arrays 1702 can be distributed about a sample container that is to be scanned along a longitudinal axis of the sample container (e.g., via the sample transporter 110 of FIG. 2).

As disclosed herein, in some examples, a sample container holding a sample is scanned by passing light through the sample container (e.g., through a side of the sample container). In some such examples, the sample container includes a cap and, thus, data about the sample is collected via sensors that are distributed about a longitudinal axis of the sample container. In other disclosed examples, the sample can be analyzed via a sample container is that does not include a cap or other covering (e.g., a decapped sample container).

FIG. 18 is a schematic side view of an example system 1800 for evaluating integrity of a sample 1802 disposed in a sample container 1804. In the example of FIG. 18, the sample container is open or decapped. The example system 1800 of FIG. 18 includes a pipettor 1806. The pipettor 1806 can be coupled to an arm 1808 controlled by a pipettor manager 1810 of an example processor 1812. The pipettor manager 1810 controls the arm 1808 to position the pipettor 1806 relative to the sample container 1804 to cause the pipettor 1806 to aspirate at least a portion of the sample 1802 from the sample container 1804.

The example system 1800 of FIG. 18 includes an emitter/sensor ring 1814 (e.g., an array). The example emitter/sensor ring 1814 includes one or more light emitters 1816 (e.g., LEDs) and one or more sensors 1818 (e.g., digital color sensor(s)). As illustrated in FIG. 19, the emitter/sensor ring 1814 is disposed relative to the sample container 1804 such that the sample container 1804 can be accessed via an opening 1900 defined by the emitter/sensor ring 1814. In the example of FIGS. 18 and 19, the pipettor 1806 accesses the sample 1802 disposed in the sample container 1804 via the opening 1900. The example emitter/sensor ring 1814 can have other shapes than illustrated in FIGS. 18 and 19. The example system 1800 of FIG. 18 can include additional emitter/sensor rings 1814 (e.g., distributed along an axis of the sample container 1804).

Referring to FIG. 18, the light emitter(s) 1816 of the emitter/sensor ring 1814 emit one or more beams 1820 of light. In the example of FIG. 18, the light emitter(s) 1816 emit the light beam(s) 1820 prior to the pipettor 1806 engaging the sample 1802 in the sample container 1804. The light beam(s) 1820 can include light having different wavelengths (e.g., wavelengths corresponding to red light, green light, or blue light), as disclosed above. In the example of FIG. 18, the light emitter(s) 1816 are coupled to the emitter/sensor ring 1814 such that a path of the light beam(s) 1820 is directed into the sample container 1804.

In the example of FIG. 18, the light beam(s) 1820 illuminate an interior 1822 of the sample container 1804. Because the sample container 1804 does not have a cap, at least a portion of the sample 1802 can be directly or substantially directly exposed to the light beam(s) 1820. The example sensor(s) 1818 of the emitter/sensor ring 1814 detect the light that is reflected by or scattered by the sample 1802.

In the example of FIG. 18, the sensor(s) 1818 are communicatively coupled to the processor 1812 via, for example, one or more wired or wireless connections. The signal data generated by the sensor(s) 1818 is transmitted to a data analyzer 1824 of the processor 1812. The example data analyzer 1824 evaluates the signal data with respect to an integrity of the sample 1802. For example, the data analyzer 1824 can detect cloudiness or turbidity of the sample 1802. As another example, the data analyzer 1824 can evaluate homogeneity of one or more layers of the sample 1802 based on the data collected by the sensor(s) 1818. As another example, the data analyzer 1824 can detect clotting (e.g., microclots) in the sample 1802 based on the detection of, for example, light scattering by the sensor(s) 1818.

Based on the analysis of the sensor data, the data analyzer 1824 determines whether the sample 1802 is acceptable for aspiration or whether the sample 1802 should be marked as an exception. Based on the analysis of sample quality, the data analyzer 1824 instructs the pipette manager 1810 with respect to a position of the pipettor 1806 relative to the sample container 1804. If the data analyzer 1824 of FIG. 18 determines that the sample 1802 is acceptable for aspiration, the pipette manager 1810 directs the arm 1808 to move the pipettor 1806 such that the pipettor 1806 passes through the opening 1900 of the emitter/sensor ring 1814 (if the pipettor 1806 has not already passed through the opening 1900) and engages at least a portion of the sample 1802 to aspirate the sample 1802. If the data analyzer 1824 of FIG. 18 determines that the sample 1802 should be marked as an exception, the pipette manager 1810 directs the arm 1808 to refrain from moving the pipettor 1806 into the interior 1822 of sample container 1804. In some examples, the pipette manager 1810 directs the arm 1808 to move the pipettor 1806 away from the sample container 1804 (e.g., and to another sample container) if the data analyzer 1824 determines that sample 1802 is an exception.

Thus, in the example of FIG. 18, a quality of the sample 1802 can be evaluated before the pipettor 1806 engages the sample 1802. Therefore, the example system 1800 reduces instances in which a poor quality sample is aspirated by the pipettor 1806. Further, the example system 1800 substantially reduces a risk of contamination of the sample 1802 by the pipettor 1806 when the sample 1802 is identified as an exception that, for example, should undergo further centrifugation before aspiration.

While an example manner of implementing the example system 1800 of FIG. 18 is illustrated in FIG. 18, one or more of the elements, processes and/or devices illustrated in FIG. 18 may be combined, divided, re-arranged, omitted, eliminated and/or implemented in any other way. Further, the example processor 1812, the example pipette manager 1810, the example data analyzer 1824, and/or, more generally, the example system 1800 of FIG. 18 may be implemented by hardware, software, firmware and/or any combination of hardware, software and/or firmware. Thus, for example, any of the example the example processor 1812, the example pipette manager 1810, the example data analyzer 1824, and/or, more generally, the example system 1800 of FIG. 18 could be implemented by one or more analog or digital circuit(s), logic circuits, programmable processor(s), application specific integrated circuit(s) (ASIC(s)), programmable logic device(s) (PLD(s)) and/or field programmable logic device(s) (FPLD(s)). When reading any of the apparatus or system claims of this patent to cover a purely software and/or firmware implementation, at least one of the example processor 1812, the example pipetter manager 1810, the example data analyzer 1824, and/or, more generally, the example system 1800 of FIG. 18 is/are hereby expressly defined to include a tangible computer readable storage device or storage disk such as a memory, a digital versatile disk (DVD), a compact disk (CD), a Blu-ray disk, etc. storing the software and/or firmware. Further still, the example system 1800 of FIG. 18 may include one or more elements, processes and/or devices in addition to, or instead of, those illustrated in FIG. 18, and/or may include more than one of any or all of the illustrated elements, processes and devices.

Figure 20:
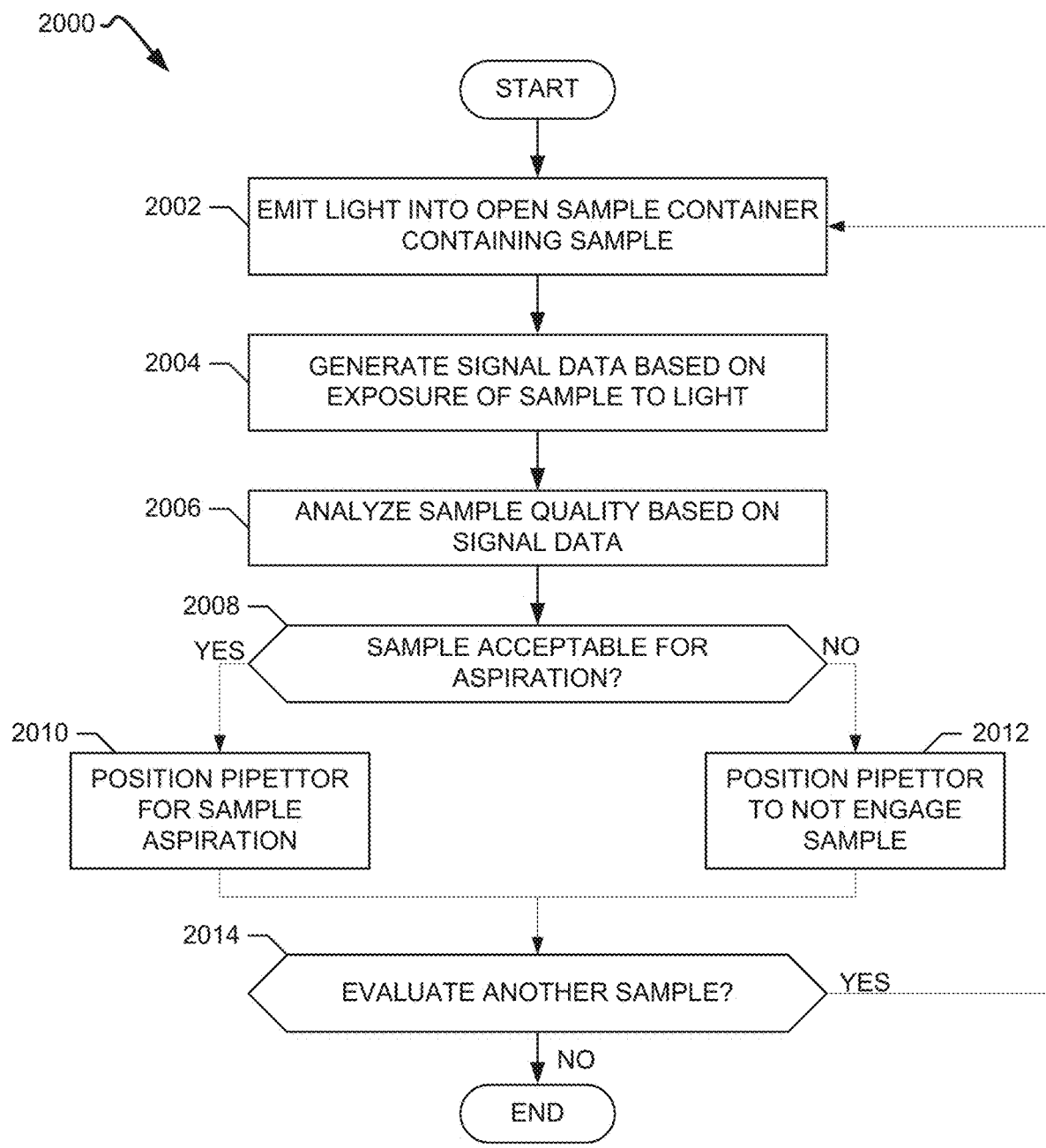
FIG. 20 is a flow diagram of another example method for evaluating sample integrity that can be used to implement the examples disclosed herein.

FIG. 20 depicts an example flow diagram representative of an example method 2000 for analyzing an integrity of a sample disposed in a sample container that does not include a cap. The example method 2000 includes emitting light into an open sample container containing a sample (block 2002). For example, the light emitter(s) 1816 of the example emitter/sensor ring 1814 of FIG. 18 emit the light beam(s) 1820, which are directed into the interior 1822 of the sample container 1804 of FIG. 18. Thus, the sample 1802 disposed in the sample container 1804 is exposed to the light beam(s) 1820.

The example method 2000 of FIG. 20 includes generating signal data based on the exposure of the sample to the light (block 2004). For example, the sensor(s) 1818 of the emitter/sensor ring 1814 of FIG. 18 detect the light reflected by or scattered by the sample 1802. The sensor(s) 1818 generate signal data based on the detection of the light.

The example method 2000 of FIG. 20 includes analyzing the sample quality based on the signal data (block 2006). For example, the data analyzer 1824 of the example processor 1812 of FIG. 18 analyzes the signal data generated by the sensor(s) 1818 of the emitter/sensor ring 1814. The data analyzer 1824 determines a quality of the sample 1802 with respect to, for example, sample color, cloudiness, homogeneity, etc.

The example method 2000 of FIG. 20 includes determining whether the sample is acceptable for aspiration (block 2008). For example, the data analyzer 1824 of FIG. 18 determines whether the sample is acceptable for aspiration or should be flagged as an exception based on the analysis of the signal data generated by the sensor(s) 1818.

If a determination is made that the sample is acceptable for aspiration, the example method of FIG. 20 includes positioning a pipettor for sample aspiration (block 2010). For example, the data analyzer 1824 instructs the pipette manager 1810 of FIG. 18 to move the arm 1808 such that the pipettor 1806 enters the interior 1822 of the sample container 1804 to engage the sample 1802.

If a determination is made that the sample is not acceptable for aspiration, the example method of FIG. 20 includes positioning the pipettor to not engage the sample (block 2012). For example, the data analyzer 1824 instructs the pipette manager 1810 of FIG. 18 to move the arm 1808 such that the pipettor 1806 moves away from the sample container 1804 and/or does not enter the interior 1822 of the sample container 1804.

The example method 2000 of FIG. 20 includes a decision of whether to evaluate another sample (block 2014). In some examples, the decision of whether to evaluate another sample occurs after a (first) sample has been identified as an exception and the (first) sample is not aspirated. In other examples, the decision of whether to evaluate another sample occurs after aspiration of a (first) sample from a (first) sample container is complete via the pipettor (e.g., the pipettor 1806 of FIG. 18). If another sample is to be evaluated, the example method 2000 continues with emitting light into a (second) open sample container containing a (second) sample (block 2002). If another sample is not to be evaluated, the example method 2000 ends.

The flowcharts of FIGS. 12 and 15 are representative of example machine readable instructions for implementing the example system 100 of FIG. 1 and the flowchart of FIG. 20 is representative of example machine readable instructions for implementing the example system 1800 of FIG. 18. In these examples, the machine readable instructions comprise program(s) for execution by a processor such as the processor 2112 shown in the example processor platform 2100 discussed below in connection with FIG. 21. The program(s) may be embodied in software stored on a tangible computer readable storage medium such as a CD-ROM, a floppy disk, a hard drive, a digital versatile disk (DVD), a Blu-ray disk, or a memory associated with the processor 2112, but the entire program(s) and/or parts thereof could alternatively be executed by a device other than the processor 2112 and/or embodied in firmware or dedicated hardware. Further, although the example program(s) are described with reference to the flowcharts illustrated in FIGS. 12, 15, and 20, many other methods of implementing the example system 100 or the example system 1800 may alternatively be used. For example, the order of execution of the blocks may be changed, and/or some of the blocks described may be changed, eliminated, or combined.

As mentioned above, the example processes of FIGS. 12, 15, and 20 may be implemented using coded instructions (e.g., computer and/or machine readable instructions) stored on a tangible computer readable storage medium such as a hard disk drive, a flash memory, a read-only memory (ROM), a compact disk (CD), a digital versatile disk (DVD), a cache, a random-access memory (RAM) and/or any other storage device or storage disk in which information is stored for any duration (e.g., for extended time periods, permanently, for brief instances, for temporarily buffering, and/or for caching of the information). As used herein, the term tangible computer readable storage medium is expressly defined to include any type of computer readable storage device and/or storage disk and to exclude propagating signals and to exclude transmission media. As used herein, "tangible computer readable storage medium" and "tangible machine readable storage medium" are used interchangeably. Additionally or alternatively, the example processes of FIGS. 12 and 15 may be implemented using coded instructions (e.g., computer and/or machine readable instructions) stored on a non-transitory computer and/or machine readable medium such as a hard disk drive, a flash memory, a read-only memory, a compact disk, a digital versatile disk, a cache, a random-access memory and/or any other storage device or storage disk in which information is stored for any duration (e.g., for extended time periods, permanently, for brief instances, for temporarily buffering, and/or for caching of the information). As used herein, the term non-transitory computer readable medium is expressly defined to include any type of computer readable storage device and/or storage disk and to exclude propagating signals and to exclude transmission media. As used herein, when the phrase "at least" is used as the transition term in a preamble of a claim, it is open-ended in the same manner as the term "comprising" is open ended.

Figure 21:
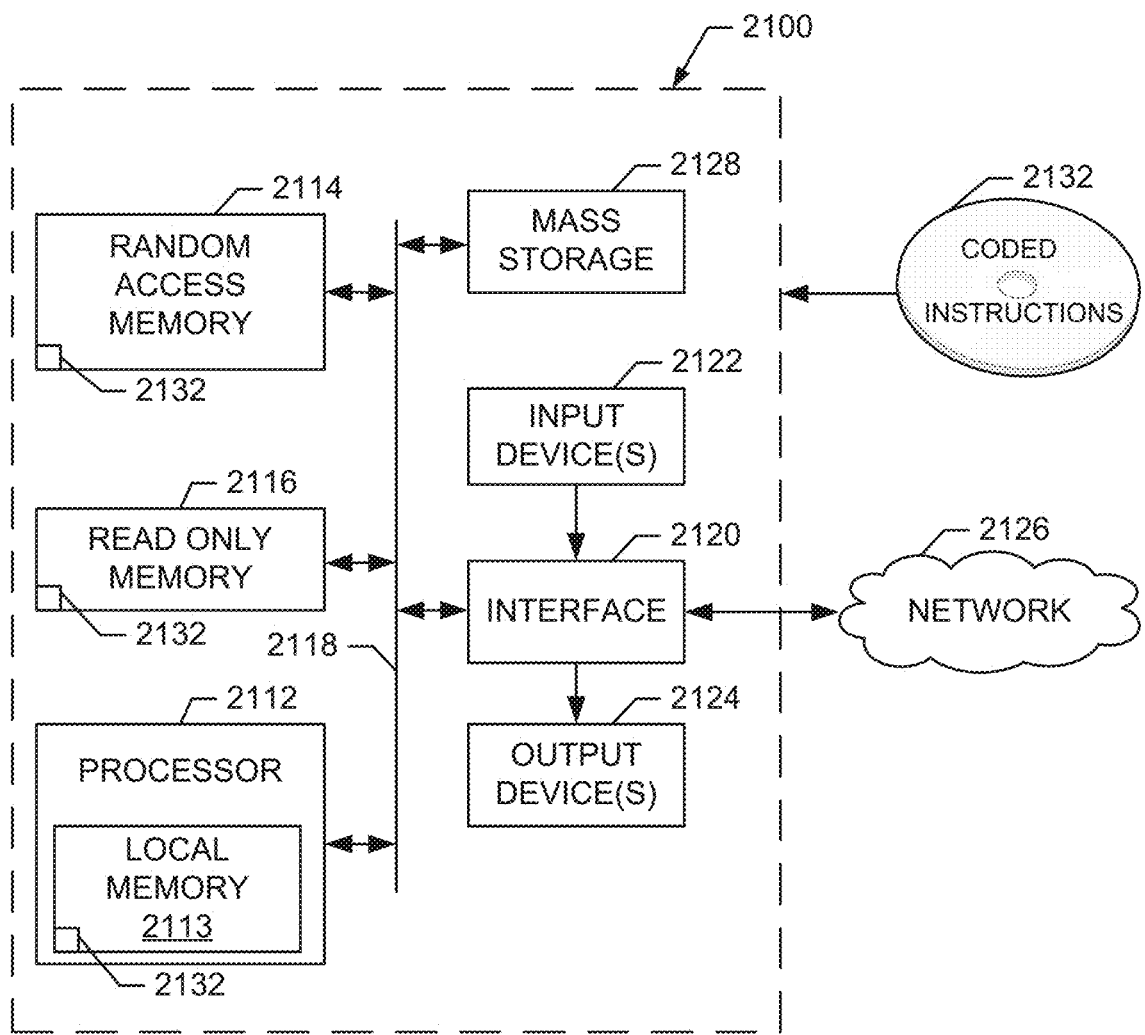
FIG. 21 is diagram of an example processor platform for use with the examples disclosed herein.

FIG. 21 is a block diagram of an example processor platform 2100 capable of executing the instructions of FIGS. 12 and 15 to implement the example system 100 of FIG. 1 and/or the instructions of FIG. 20 to implement the example system 1800 of FIG. 18. The processor platform 2100 can be, for example, a server, a personal computer, a mobile device (e.g., a cell phone, a smart phone, a tablet such as an iPad™), a personal digital assistant (PDA), an Internet appliance, or any other type of computing device.

The processor platform 2100 of the illustrated example includes a processor 2112. The processor 2112 of the illustrated example is hardware. For example, the processor 2112 can be implemented by one or more integrated circuits, logic circuits, microprocessors or controllers from any desired family or manufacturer.

The processor 2112 of the illustrated example includes a local memory 2113 (e.g., a cache). The processor 2112 of the illustrated example is in communication with a main memory including a volatile memory 2114 and a non-volatile memory 2116 via a bus 2118. The volatile memory 2114 may be implemented by Synchronous Dynamic Random Access Memory (SDRAM), Dynamic Random Access Memory (DRAM), RAMBUS Dynamic Random Access Memory (RDRAM) and/or any other type of random access memory device. The non-volatile memory 2116 may be implemented by flash memory and/or any other desired type of memory device. Access to the main memory 2114, 2116 is controlled by a memory controller.

The processor platform 2100 of the illustrated example also includes an interface circuit 2120. The interface circuit 2120 may be implemented by any type of interface standard, such as an Ethernet interface, a universal serial bus (USB), and/or a PCI express interface.

In the illustrated example, one or more input devices 2122 are connected to the interface circuit 2120. The input device(s) 2122 permit(s) a user to enter data and commands into the processor 2112. The input device(s) can be implemented by, for example, an audio sensor, a microphone, a camera (still or video), a keyboard, a button, a mouse, a touchscreen, a track-pad, a trackball, isopoint and/or a voice recognition system.

One or more output devices 2124 are also connected to the interface circuit 2120 of the illustrated example. The output devices 2124 can be implemented, for example, by display devices (e.g., a light emitting diode (LED), an organic light emitting diode (OLED), a liquid crystal display, a cathode ray tube display (CRT), a touchscreen, a tactile output device, a printer and/or speakers). The interface circuit 2120 of the illustrated example, thus, typically includes a graphics driver card, a graphics driver chip or a graphics driver processor.

The interface circuit 2120 of the illustrated example also includes a communication device such as a transmitter, a receiver, a transceiver, a modem and/or network interface card to facilitate exchange of data with external machines (e.g., computing devices of any kind) via a network 2126 (e.g., an Ethernet connection, a digital subscriber line (DSL), a telephone line, coaxial cable, a cellular telephone system, etc.).

The processor platform 2100 of the illustrated example also includes one or more mass storage devices 2128 for storing software and/or data. Examples of such mass storage devices 2128 include floppy disk drives, hard drive disks, compact disk drives, Blu-ray disk drives, RAID systems, and digital versatile disk (DVD) drives.

Coded instructions 2132 to implement the methods of FIGS. 12, 15, and/or 20 may be stored in the mass storage device 2128, in the volatile memory 2114, in the non-volatile memory 2116, and/or on a removable tangible computer readable storage medium such as a CD or DVD.

From the foregoing, it will be appreciated that the above disclosed systems and methods provide for automated evaluation of sample integrity of a sample disposed in a sample container. The disclosed examples assess the quality of the sample with respect to, for example, HIL without requiring the sample to be aspirated from the sample container and disposed in an analyzer to measure color absorption. The disclosed examples further substantially eliminate the need for visual inspection of the sample and sample container by laboratory personnel by outputting an indication of sample quality for further processing that is viewable by a user via a graphical user interface. Thus, the disclosed examples reduce processing time and costs and prevent introduction of laboratory personnel bias into the analysis of the quality of the sample for further processing.

Further, the disclosed examples determine sample integrity for samples in sample containers having one or more labels affixed to an outer surface of the sample container. The disclosed examples automatically detect the presence of the one or more labels based on signal data collected from scanning a length of the sample container and restore the signal data affected by the label(s) using a signal restoration coefficient. As a result, the disclosed examples correct for the presence of the label(s) to generate digital representations of the sample and/or the sample container that are substantially similar to sample representations that would be generated if there were no labels on the sample container. In accounting for the presence of the label(s) by automatically restoring the affected signal data, the disclosed examples provide for a flexible and efficient analysis of samples and sample containers without requiring the sample container to be inserted in a certain position to avoid interference from the label(s).

Although certain example methods, apparatus and articles of manufacture have been disclosed herein, the scope of coverage of this patent is not limited thereto. On the contrary, this patent covers all methods, apparatus and articles of manufacture fairly falling within the scope of the claims of this patent.

What is claimed is:

1. A method comprising:
    scanning, by executing an instruction with a processor, a sample container having a sample disposed therein to generate signal data including a first signal portion and a second signal portion;

detecting, by executing an instruction with the processor, if the sample container includes a label attached to a surface of the sample container based on the second signal portion;

if the sample container includes a label, applying, by executing an instruction with processor, an adjustment factor to the second signal portion to create adjusted signal data; and determining, by executing an instruction with the processor, a property of the sample based on one or more of the first signal portion or the adjusted signal data.

2. The method of claim 1, further including assigning a quality indicator to the sample based on the property of the sample.

3. The method of claim 1, wherein the property is one of a level of hemolysis, icterus, or lipemia in the sample.

4. The method of claim 1, further including generating a representation of the sample based on the adjusted signal data.

5. The method of claim 4, wherein the property is a sample color and the representation includes the property.

6. The method of claim 1, wherein detecting if the sample container includes a label includes:

identifying attenuated signal data in the second signal portion;

determining if the attenuated signal data is below a predetermined threshold; and if the attenuated signal data is below the threshold, determining that the sample container includes the label.

7. The method of claim 6, further including determining a number of labels on the sample container based on the attenuated signal data relative to non-attenuated signal data for the sample container or a second sample container.

8. The method of claim 1, wherein the first signal portion and the second signal portion are substantially the same.

9. A method comprising:

scanning, by executing an instruction with a processor, a sample container to generate signal data, at least a portion of the sample container containing a sample;

detecting, by executing an instruction with the processor, an attenuated portion in the signal data;

restoring, by executing an instruction with the processor, the attenuated portion of the signal data to generate a restored portion; and determining, by executing an instruction with the processor, a property of the sample based on the signal data including the restored portion.

10. The method of claim 9, wherein restoring the attenuated portion of the signal data includes:

identifying a value in at least one of the attenuated portion or the signal data not including the attenuated portion;

performing a comparison of the value to previously known values stored in a database;

identifying a signal restoration coefficient based on the comparison; and applying the signal restoration coefficient to the attenuated portion to generate the restored portion.

11. The method of claim 9, further including interpolating the restored portion in the signal data.

12. The method of claim 9, wherein the signal data includes first signal data corresponding to a first color and second signal data corresponding to a second color, and restoring the attenuated portion of the signal data includes restoring a first attenuated portion in the first signal data and restoring a second attenuated portion in the second signal data.

13. The method of claim 9, wherein the scanning includes exposing at least a portion of the sample container to a light source and further including:

determining a luminance percentage of an output of the light source; and generating a representation of the sample based on the signal data, the restored portion, and the luminance percentage.

14. A system comprising:

a scanner to scan a sample container having a sample disposed therein, the scan to generate signal data; and a processor to:

detect a presence of a label on the sample container based on attenuated data in the signal data;

restore at least a portion of the attenuated data in the signal data based on the detection of the label to create a restored portion of the signal data; and identify the sample as a routine sample or as an exception based on the signal data including the restored portion of the signal data.

15. The system of claim 14, wherein the scanner is to:

identify a position of a cap coupled to the sample container based on the signal data; and move the sample container to expose the cap of the sample container to a light source; and wherein the processor is to determine a color of the cap.

16. The system of claim 14, wherein the processor is to:

generate an indicator representing the sample as being a routine sample or an exception; and output the indicator for viewing via a graphical user interface.

17. The system of claim 14, wherein the processor is to restore the portion of the signal data by:

comparing the portion of the signal data to calibration data;

determining a signal restoration coefficient based on the comparison; and applying the signal restoration coefficient to the portion to generate the restored portion.

18. The system of claim 14, wherein the signal data is indicative of a color of the sample and the processor is to:

analyze one or more of a hemolysis level, an icterus level, or a lipemia level in the sample based on the color of the sample; and identify the sample as an exception if at least one of the hemolysis level, the icterus level, or the lipemia level is above a respective threshold.

19. The system of claim 14, wherein the signal data is indicative of a color of the sample and the processor is to:

identify a first layer in the sample and a second layer in the sample based on the color of the sample; and identify the sample as an exception based on a color of one or more of the first layer, the second layer, or a border between the first layer and the second layer.

20. The system of claim 14, wherein the processor is to detect the presence of the label on the sample container by:

identifying a change in a first portion of the signal data relative to a second portion of the signal data; and detecting the presence of a label on the sample container based on the identification of the change in the first portion of the signal data.

\* \* \* \* \*